United States Patent
Li et al.

(10) Patent No.: US 11,158,821 B2
(45) Date of Patent: Oct. 26, 2021

(54) ORGANIC ELECTROLUMINESCENT DEVICE AND MANUFACTURING METHOD THEREOF

(71) Applicants: Kunshan New Flat Panel Display Technology Center Co., Ltd., Kunshan (CN); KunShan Go-Visionox Opto-Electronics Co., Ltd., Kunshan (CN)

(72) Inventors: Weiwei Li, Kunshan (CN); Fei Zhao, Kunshan (CN); Chao Min, Kunshan (CN); Song Liu, Kunshan (CN); Wei Ao, Kunshan (CN); Yucheng Liu, Kunshan (CN)

(73) Assignees: Kunshan New Flat Panel Display Technology Center Co., Ltd., Jiangsu (CN); KunShan Go-Visionox Opto-Electronics Co., Ltd, Jiangsu (CN)

( * ) Notice: Subject to any disclaimer, the term of this patent is extended or adjusted under 35 U.S.C. 154(b) by 399 days.

(21) Appl. No.: 16/317,491

(22) Filed: Jan. 11, 2019

(65) Prior Publication Data

US 2019/0165286 A1    May 30, 2019

Related U.S. Application Data

(63) Continuation of application No. PCT/CN2018/073380, filed on Jan. 19, 2018.

(30) Foreign Application Priority Data

Jan. 20, 2017 (CN) .......................... 201710048295.3

(51) Int. Cl.
   *H01L 51/50* (2006.01)
   *H01L 51/00* (2006.01)
   (Continued)

(52) U.S. Cl.
   CPC ........ *H01L 51/0094* (2013.01); *H01L 51/001* (2013.01); *H01L 51/0069* (2013.01);
   (Continued)

(58) Field of Classification Search
   None
   See application file for complete search history.

(56) References Cited

U.S. PATENT DOCUMENTS

2005/0142379 A1* 6/2005 Juni .................... H01L 51/5275
                                                              428/690
2017/0012207 A1   1/2017 Seo et al.

FOREIGN PATENT DOCUMENTS

CN    103515537 A    1/2004
CN    1303083 C      3/2007
(Continued)

OTHER PUBLICATIONS

European search report for European application No. 18741504.7 dated Jan. 3, 2020.
(Continued)

*Primary Examiner* — Gregory D Clark

(57) ABSTRACT

The present application provides an organic electroluminescent device and a manufacturing method thereof. A host material of a light-emitting layer of the organic electroluminescent device is co-evaporated by a donor host material and a acceptor host material in a same evaporation source to form an exciplex, which solves the technical problems such as low luminous efficiency, short service life or complicated operation process of the organic electroluminescent device in the prior art. The organic electroluminescent device according to the present application includes an anode, a cathode and a light-emitting layer disposed between the anode and the cathode, a host material of the light-emitting layer is formed by premixing a donor host material and a acceptor host material, the donor host material and the
(Continued)

acceptor host material are co-evaporated in a same evaporation source to form an exciplex, and the host material is doped with a guest material.

16 Claims, 2 Drawing Sheets

(51) Int. Cl.
  *H01L 51/56* (2006.01)
  *H01L 51/52* (2006.01)
(52) U.S. Cl.
  CPC ...... *H01L 51/0071* (2013.01); *H01L 51/0072* (2013.01); *H01L 51/50* (2013.01); *H01L 51/5004* (2013.01); *H01L 51/5016* (2013.01); *H01L 51/5056* (2013.01); *H01L 51/5088* (2013.01); *H01L 51/5096* (2013.01); *H01L 51/52* (2013.01); *H01L 51/56* (2013.01); *H01L 51/007* (2013.01); *H01L 51/0065* (2013.01); *H01L 51/0067* (2013.01); *H01L 51/0068* (2013.01); *H01L 2251/308* (2013.01); *H01L 2251/552* (2013.01); *H01L 2251/556* (2013.01)

(56) References Cited

FOREIGN PATENT DOCUMENTS

| CN | 104600213 | A | | 5/2015 | |
| CN | 105789468 | A | | 7/2016 | |
| CN | 105895811 | | * | 8/2016 | ............. H01L 51/50 |
| CN | 105895811 | A | | 8/2016 | |
| CN | 105957971 | A | | 9/2016 | |
| CN | 106328816 | A | | 1/2017 | |
| JP | 2012-195517 | A | | 10/2012 | |
| JP | 2013-530515 | A | | 7/2013 | |
| JP | 2014-187130 | A | | 10/2014 | |
| JP | 2016-039143 | A | | 3/2016 | |
| JP | 2016-171319 | A | | 9/2016 | |
| KR | 20150105906 | A | | 9/2015 | |
| KR | 10-2016-0055822 | A | | 5/2016 | |
| KR | 10-2016-0143678 | A | | 12/2016 | |
| WO | 2011136755 | A1 | | 11/2011 | |
| WO | 2015180524 | A1 | | 12/2015 | |
| WO | 2016042997 | A | | 3/2016 | |
| WO | 2016107537 | A | | 7/2016 | |
| WO | 2016-158363 | A | | 10/2016 | |
| WO | 2017006222 | A | | 1/2017 | |

OTHER PUBLICATIONS

Chinese Second Office Action for CN Application No. 201710048295.3 dated Aug. 12, 2019.
PCT International Search Report dated Apr. 20, 2018 in International Application No. PCT/CN2018/073380, Includes English Translation. 6 pages.
Chinese Third Office Action for CN Application No. 201710048295.3 dated Aug. 12, 2019.
Taiwan First Office Action for Application No. 107101972 dated Jan. 4, 2019.
Korean First Office Action for Application No. 10-2019-7015666 dated Mar. 27, 2020.
Japanese First Office Action for Application No. 2019-529234 dated Jun. 16, 2020.
Japanese Second Office Action for Application No. 2019-529234 dated Oct. 13, 2020.
Written Opinion of PCT/CN2018/073380 dated Apr. 20, 2018.

* cited by examiner

ORGANIC ELECTROLUMINESCENT DEVICE AND MANUFACTURING METHOD THEREOF

CROSS-REFERENCE TO RELATED APPLICATIONS

The present application is a continuation of International Patent Application No. PCT/CN2018/073380 filed on Jan. 19, 2018, which claims priority to Applicant's patent application, which is filed on Jan. 20, 2017, with the application No. 201710048295.3, entitled "Organic Electroluminescent Device." The entire contents of the above application are incorporated herein by reference in their entirety.

TECHNICAL FIELD

The present application relates to the display device technical field, in particular to an organic electroluminescent device and a manufacturing method thereof.

BACKGROUND

The organic electroluminescent device is a self-luminous device, and has been widely concerned as a next-generation flat panel display device because of its wide viewing angle, high contrast, high brightness, low driving voltage, fast response time, and thin and light panel, etc.

The light-emitting mechanism of the organic electroluminescent device belongs to a carrier injection type, that is, when a voltage is applied to a light-emitting layer sandwiched between an anode and a cathode, holes injected from the anode flow through a hole transport layer to the light-emitting layer, and electrons injected from the cathode flow through an electron transport layer to the light-emitting layer. Holes and electrons as carriers are combined in the light-emitting layer to excite the light-emitting substance, and the luminescence occurs when the excited state is relaxed to a ground state. However, studies have shown that the electron mobility of the electron transport layer is much lower than the hole mobility of the hole transport layer, which leads to the imbalance of positive and negative carriers transport, and seriously affects the luminous efficiency and service life of the organic electroluminescent device.

In order to adjust the balance of carriers of the light-emitting layer, a dual-host material mixed by an electron-biased electron-type (electron-accepting) host material and a hole-biased hole-type (electron-donating) host material may be generally used by a light-emitting layer of a top-emitting organic electroluminescent device. In the prior art, the co-evaporation way of the two kinds of materials is commonly adopted, but the two kinds of materials are required to be respectively placed in two evaporation sources for evaporation, which has high requirements on the mass production process and affects the yield of the mass production. However, if the common electron-type host BAlq or hole-type host CBP is adopted as the host, the carriers cannot be balanced, and the luminous efficiency of the device may be reduced.

In order to solve the above problems, a method of using a bipolar single host material has been developed in the industry. Although the organic electroluminescent device based on this luminescent material can adjust the carrier balance to a certain extent, generally the efficiency is still relatively low, the lifetime still needs to be improved, and the problem of serious roll-off also needs to be solved.

SUMMARY

In view of this, embodiments of the present application provide an organic electroluminescent device and a manufacturing method thereof, a host material of a light-emitting layer of the organic electroluminescent device is co-evaporated by a donor host material and a acceptor host material in a same evaporation source to form an exciplex, which solves the technical problems such as low luminous efficiency, short service life or complicated operation process of the organic electroluminescent device in the prior art.

An organic electroluminescent device according to an embodiment of the present application includes an anode, a cathode and a light-emitting layer disposed between the anode and the cathode, a host material of the light-emitting layer is formed by premixing a donor host material and a acceptor host material, the donor host material and the acceptor host material are co-evaporated in a same evaporation source to form an exciplex, and the host material is doped with a guest material.

In the organic electroluminescent device according to the embodiments of the present application, the host material of the light-emitting layer is co-evaporated by a donor host material and a acceptor host material in a same evaporation source to form an exciplex, thus not only can the balance between the electron and hole carriers be facilitated, the lifetime and efficiency of the device be improved, but also the difficulty of process operation is reduced and the yield of mass production is improved by the single-source evaporation. In addition, the exciplex is formed by the two host materials, and is used as a medium to efficiently transfer the triplet energy to a guest material through FRET energy transfer, so that the deactivation of the excitation energy is restrained, the problem of the serious roll-off drop under high brightness is solved effectively, the stability of the device is further improved, and at the same time, the doping concentration of the guest material is reduced, which reduces the product cost.

DETAILED DESCRIPTION

In the following description, the technical scheme in the embodiments of the present application will be described clearly and completely in conjunction with the accompanying drawings. Obviously, the described embodiments are only a part of the embodiments of the present application, not all of the embodiments. Based on the embodiments of the present application, all other embodiments obtained by those skilled in the art without any creative work are within the protection scope of the present application.

Figure 1:
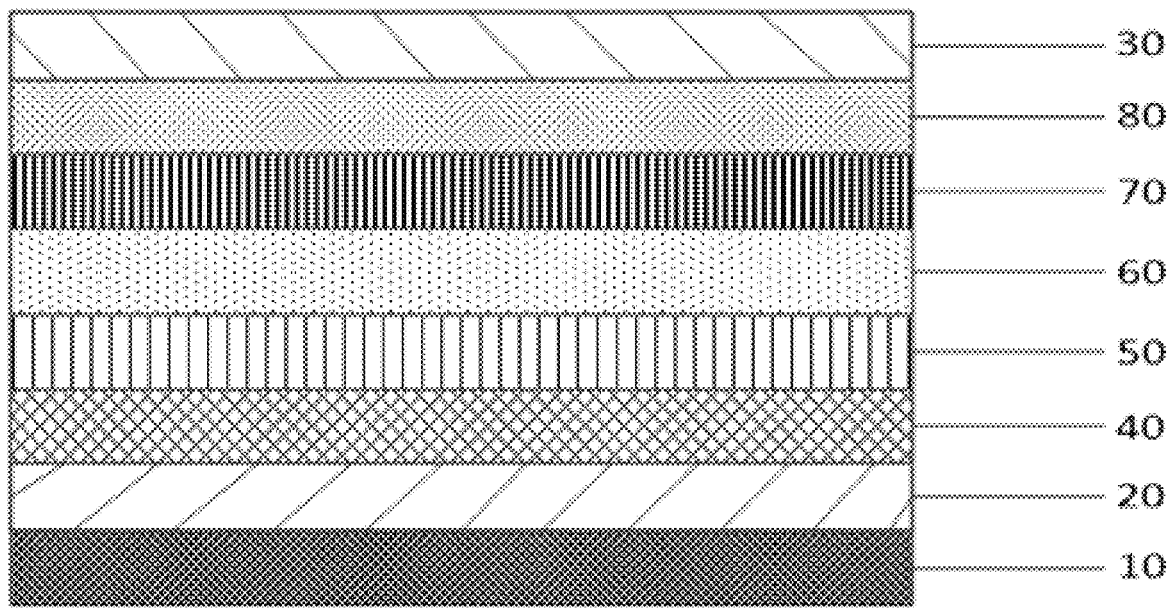
FIG. 1 is a schematic diagram illustrating an organic electroluminescent device according to an embodiment of the present application.

FIG. 1 is a schematic diagram illustrating an organic electroluminescent device provided with a light-emitting layer between an anode and a cathode according to an embodiment of the present application. As shown in FIG. 1, the organic electroluminescent device includes a substrate 10, an anode 20 disposed on the substrate 10, a hole injection layer (HIL) 40, a hole transport layer (HTL) 50, a light-emitting layer 60, an electron transport layer (ETL) 70 and an electron injection layer (EIL) 80 which are sequentially stacked on the anode 20, and a transparent cathode 30.

A host material of the light-emitting layer 60 is formed by premixing a donor host material and an acceptor host material, the donor host material and the acceptor host material are co-evaporated in a same evaporation source to form an exciplex, and the host material is doped with a guest material. In an embodiment, the guest material is preferably a phosphorescent material, i.e., the phosphorescent material is dispersed in the dual-host material as the guest material, which can make the light-emitting device has high luminous efficiency.

In an embodiment of the present application, the donor host and the acceptor host belong to different series of derivatives, wherein the donor host is selected as a hole-biased hole-type material, such as an ammonia compound, and the acceptor host is selected as an electron-biased electron-type material, such as a phosphorus compound. Both evaporation temperatures of the donor host and the acceptor host are 150° C.~500° C., and glass transition temperatures $T_g$ are greater than 100° C.

In an embodiment of the present application, an absolute value of a difference between evaporation temperatures of the donor host and the acceptor host is less than 30° C. In a preferred embodiment, the absolute value of the difference between the evaporation temperatures of the donor host and the acceptor host is less than 15° C. In a more preferred embodiment, the absolute value of the difference between the evaporation temperatures of the two is less than 5° C. That is, the evaporation temperatures and the glass transition temperatures of the donor host and the acceptor host are within a same range, and the smaller the difference between the evaporation temperatures of the two, the more favorable it is to place them in the same evaporation source for co-evaporation (i.e., single-source evaporation), thus not only can the balance between the electron and hole carriers be facilitated, the lifetime and efficiency of the device be improved, but also the difficulty of process operation is reduced and the yield of mass production is improved by the single-source evaporation.

The exciplex is formed during the donor host and the acceptor host are co-evaporated into a thin film. In an embodiment of the present application, a triplet energy level of the donor host is greater than a singlet energy level of the exciplex, an energy gap between the two is greater than or equal to 0.2 eV, and an absolute value of HOMO energy level of the donor host is less than or equal to 5.3 eV; a triplet energy level of the acceptor host is greater than a singlet energy level of the exciplex, an energy gap between the two is greater than 0.2 eV, and an absolute value of LUMO energy level of the acceptor host is greater than 2.0 eV. That is, in the host material of the embodiments of the present application, the energy level relationship between the donor host and the acceptor host, and the exciplex formed thereby satisfies the following conditions:

$T_1^D - S_1 \geq 0.2$ eV $T_1^A - S_1 > 0.2$ eV $|HOMO_D| \leq 5.3$ eV $|LUMO_A| > 2.0$ Ev.

Among them, $T_1^D$ represents the triplet energy level of the donor, $T_1^A$ represents the triplet energy level of the acceptor, $S_1$ represents the singlet energy level of the exciplex, $HOMO_D$ represents the HOMO energy level of the donor, and $LUMO_A$ represents the LUMO energy level of the acceptor.

When the two host materials satisfy the above four conditions, the exciplex formed is a thermally activated delayed fluorescence exciplex (TADF exciplex), which is a material with a small energy level difference ($\Delta EST<0.3$ eV) between a first singlet state and a first triplet state, and has a thermally activated delayed fluorescence effect.

Figure 2:
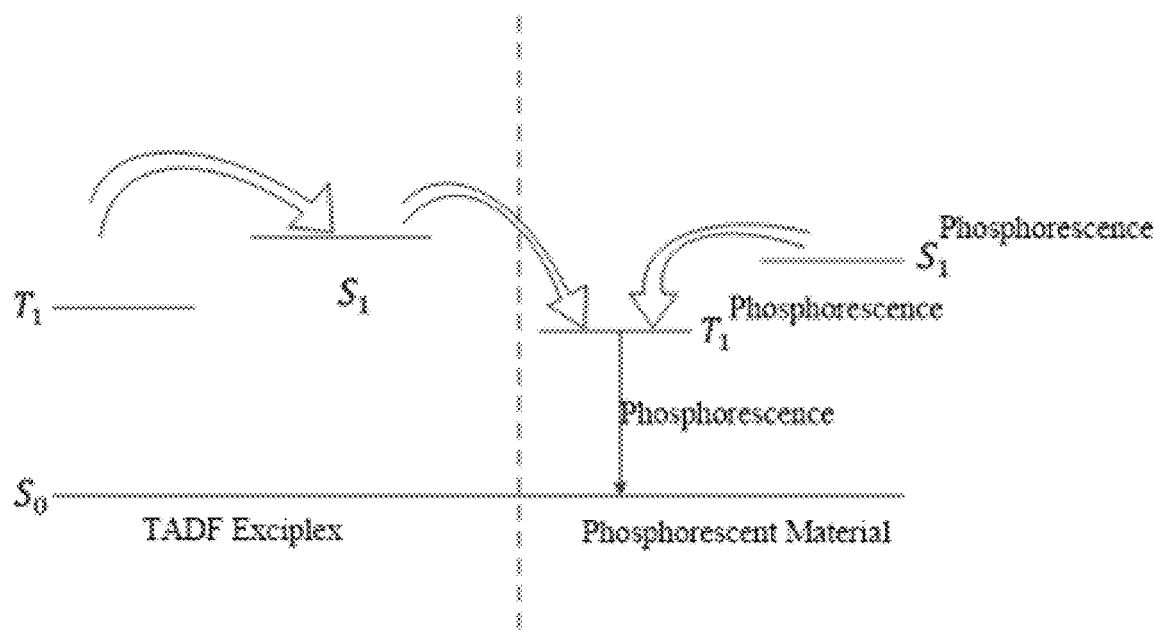
FIG. 2 is a schematic diagram illustrating energy transfer of a light-emitting layer in an organic electroluminescent device according to an embodiment of the present application.

As shown in FIG. 2, in the TADF exciplex formed by the dual-host material according to the embodiments of the present application, the triplet energy is transferred to the singlet state through the inverse intersystem crossing, and then transferred to the phosphorescent material through Förster energy; at the same time, the energy of the phosphorescent material itself is also transferred from the singlet state to the triplet state. In this way, the triplet energy of the host material and the guest material in the device is efficiently transferred to the phosphorescent material and fully utilized, thereby the efficiency of the device is improved; and the deactivation of the excitation energy (luminescence or thermal-deactivation) is restrained by the fast energy conversion process of the thermally activated delayed fluorescence, the problem of the serious roll-off drop under high brightness is solved effectively, the stability of the device is further improved, and the lifetime of the light-emitting device is prolonged. In addition, since the short-range Dexter energy transfer is performed in the exiting phosphorescent system, it is necessary to increase the doping concentration of the phosphorescent material to ensure the sufficient energy transfer. However, in the light-emitting device according to the embodiments of the present application, the doping concentration of the phosphorescent material can be reduced through the long-range Förster energy transfer, thus the product cost is reduced.

As a donor host material, in an embodiment of the present application, a molecular formula of the donor host material is:

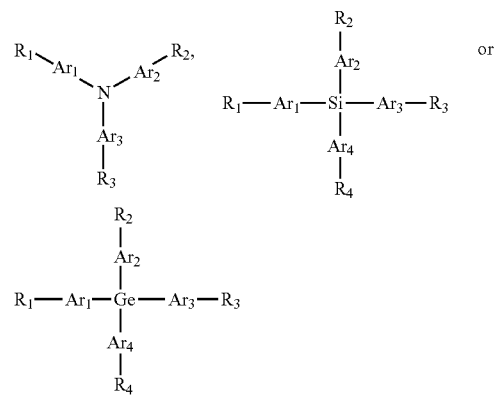

wherein $Ar_1$, $Ar_2$, $Ar_3$ and $Ar_4$ substituents are the same or different, and are independently selected from an arylene group or a heteroarylene group (a hetero atom specifically refers to a nitrogen atom); and structures of $R_1$, $R_2$, $R_3$ and $R_4$ are

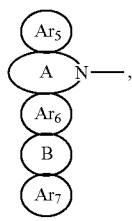

wherein $Ar_5$, A, $Ar_6$, B and $Ar_7$ are connected in a fused ring manner, sharing two atoms, $Ar_5$, $Ar_6$ and $Ar_7$ are the same or different, and are independently selected from a benzene ring, a substituted benzene ring, a naphthalene ring, a substituted naphthalene ring, an anthracene ring or a substituted anthracene ring, A is a five-membered heterocyclic ring or a six-membered heterocyclic ring containing nitrogen atoms, and B is a five-membered ring, a five-membered heterocyclic ring, a six-membered ring or a six-membered heterocyclic ring (the hetero atom is one or both of a nitrogen atom, an oxygen atom, a sulfur atom or a selenium atom).

As an acceptor host material, in an embodiment of the present application, a molecular formula of the acceptor host material is:

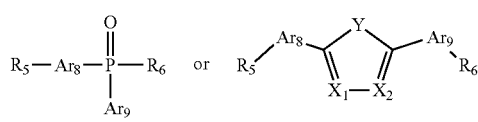

wherein $X_1$ and $X_2$ are the same or different, and are —CH— or —N— respectively;

Y is —O—, —S—, —Se—, —C(CH$_3$)$_2$—, —C(C$_6$H$_5$)$_2$— or —C(9-fluorenyl)-;

$Ar_8$ and $Ar_9$ substituents are the same or different, and are independently selected from an arylene group or a heteroarylene group (a hetero atom specifically refers to a nitrogen atom); and structures of $R_5$ and $R_6$ are

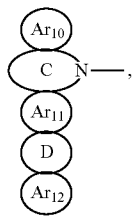

wherein $Ar_{10}$, C ring, $Ar_{11}$, D ring and $Ar_{12}$ are connected in a fused ring manner, sharing two atoms, $Ar_{10}$, $Ar_{11}$ and $Ar_{12}$ are the same or different, and are independently selected from a benzene ring, a substituted benzene ring, a naphthalene ring or a substituted naphthalene ring, C ring is a five-membered heterocyclic ring or a six-membered heterocyclic ring containing nitrogen atoms, and D ring is a five-membered ring, a five-membered heterocyclic ring, a six-membered ring or a six-membered heterocyclic ring (the hetero atom is one or both of a nitrogen atom, an oxygen atom, a sulfur atom or a selenium atom).

Preferably, the $R_1$, $R_2$, $R_3$, $R_4$, $R_5$ and $R_6$ heterocyclic rings are independently selected from any one of the following molecular structures:

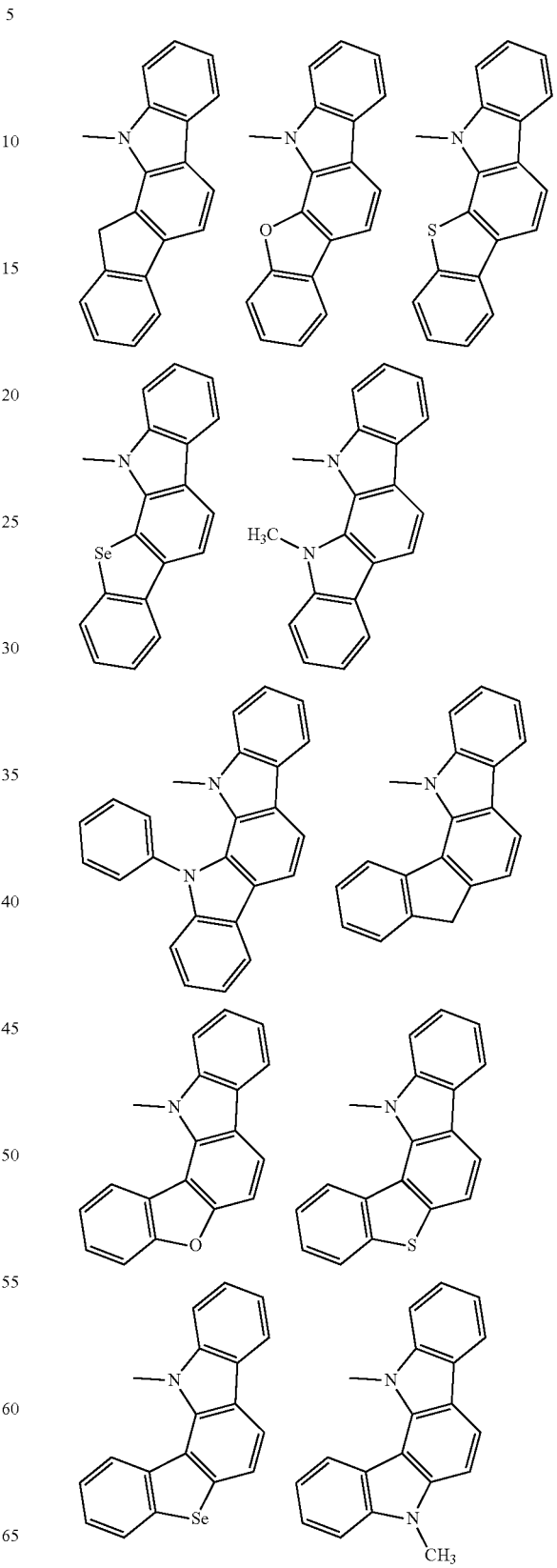

-continued
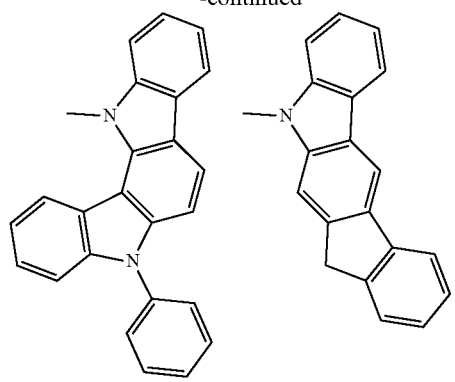
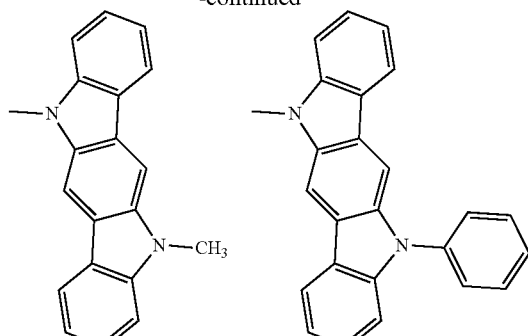
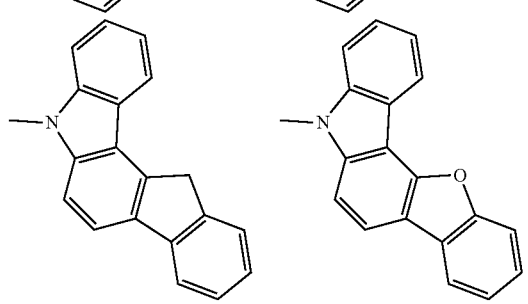
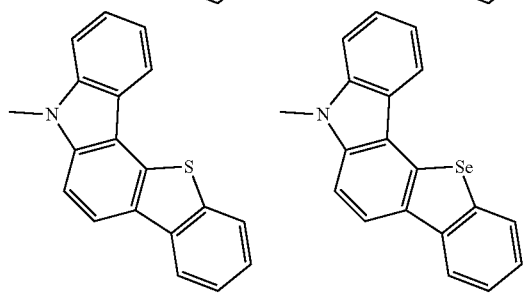
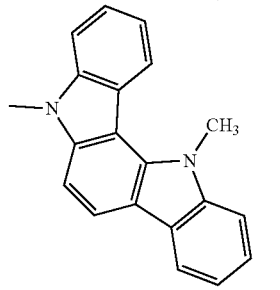
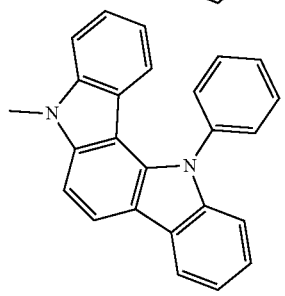
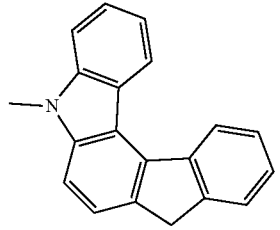

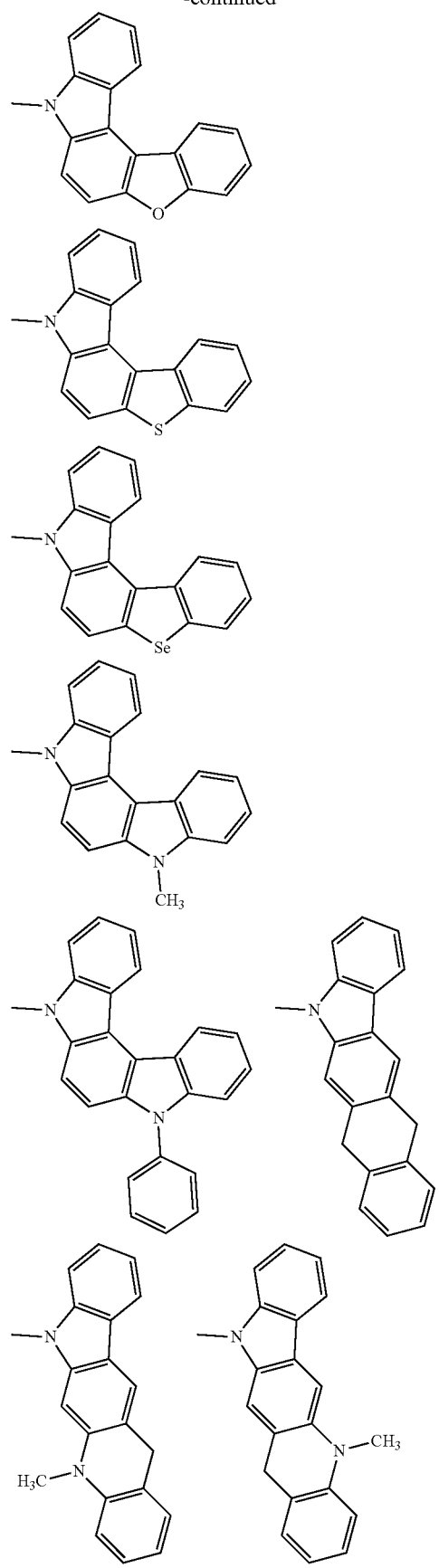
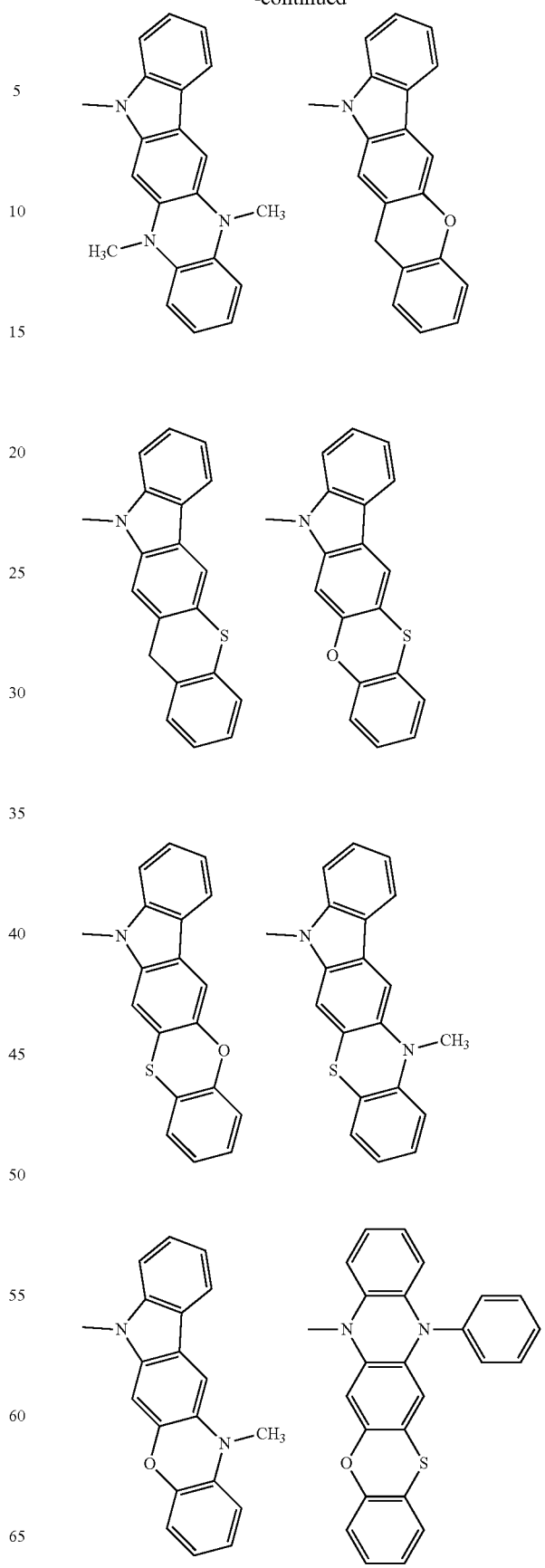

-continued
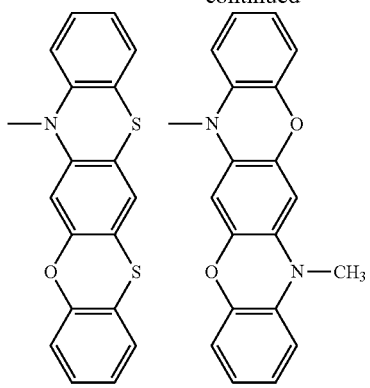
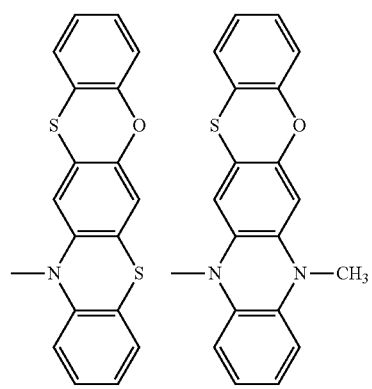
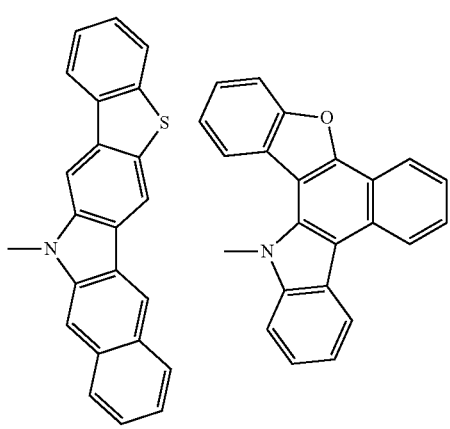
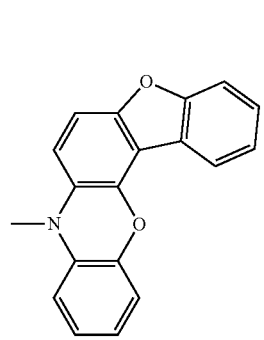
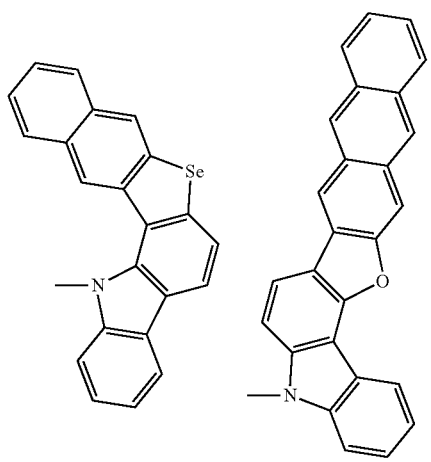
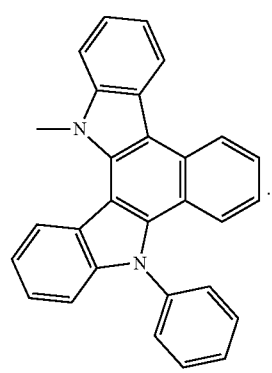

Further preferably, the donor host material is a compound with the following structures:
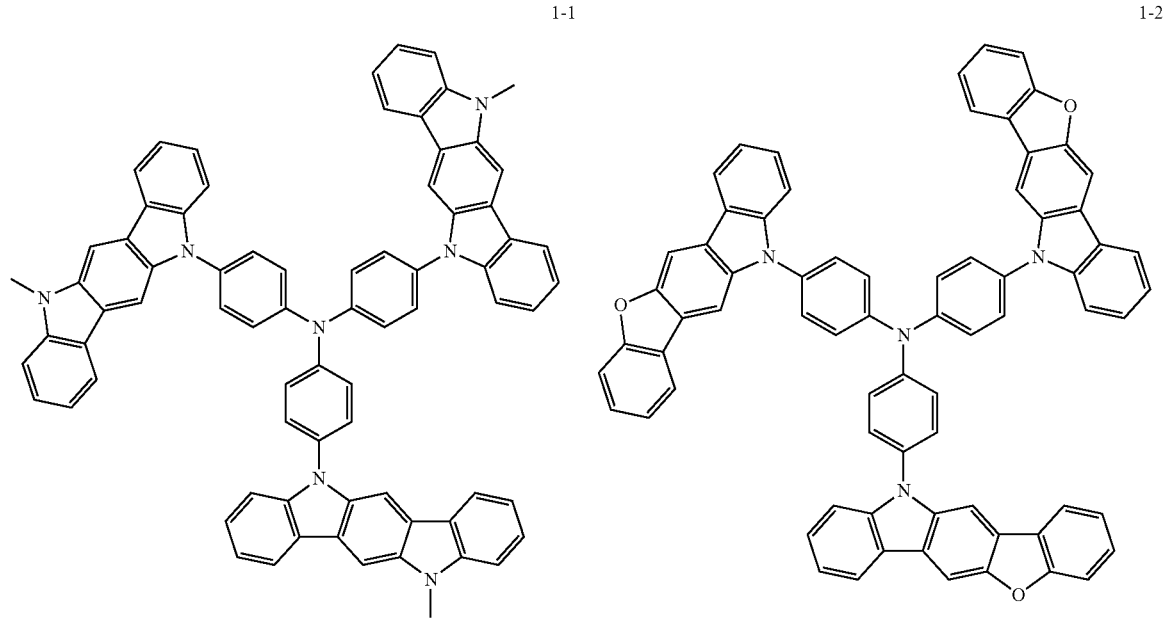
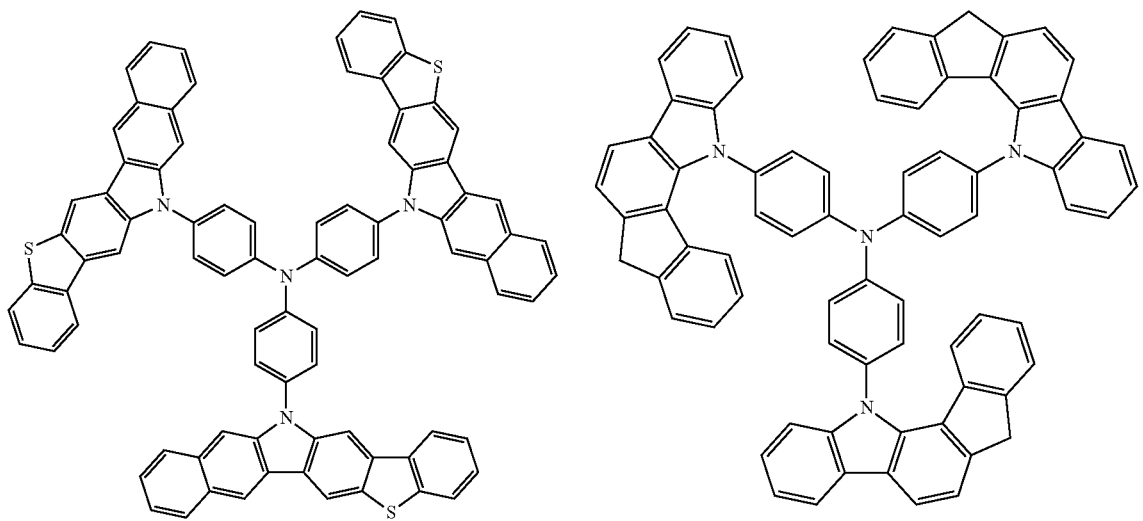

1-5
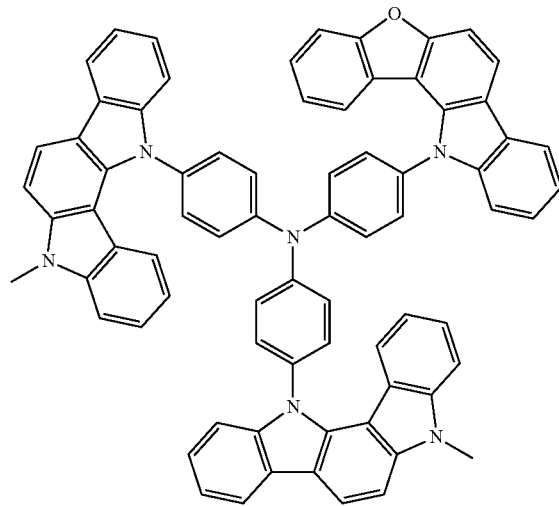
1-6
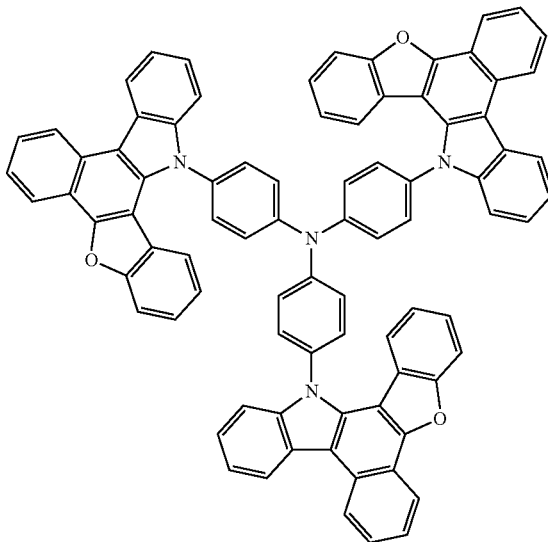
1-7
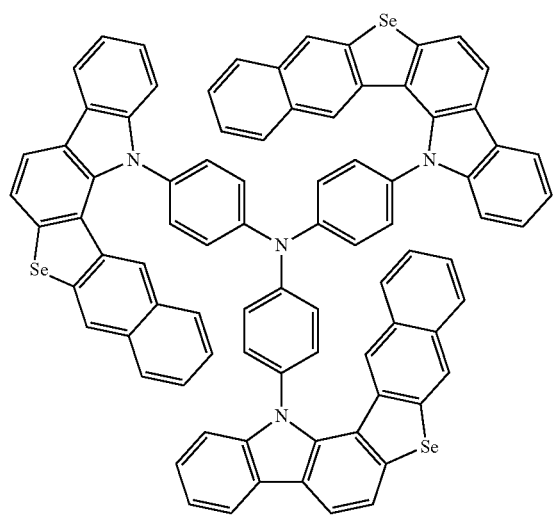
1-8
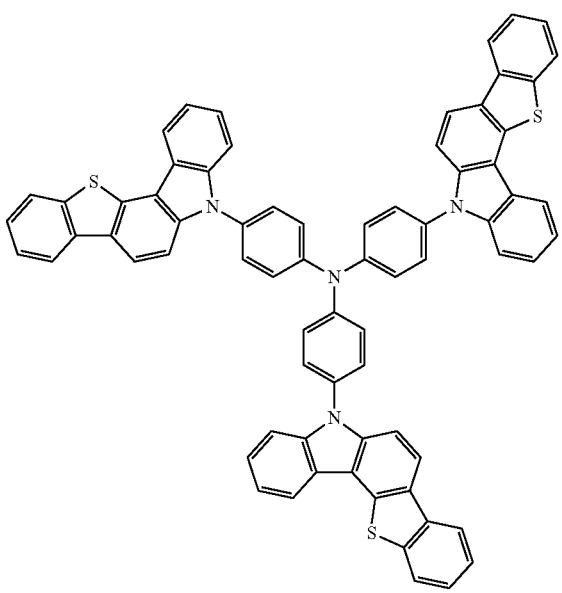

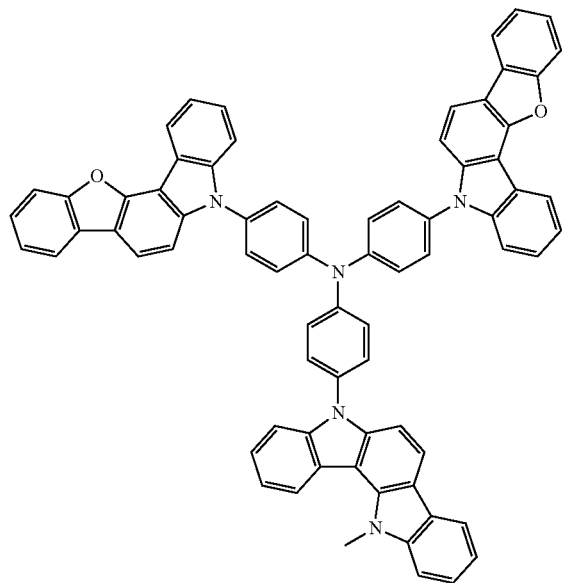
1-9
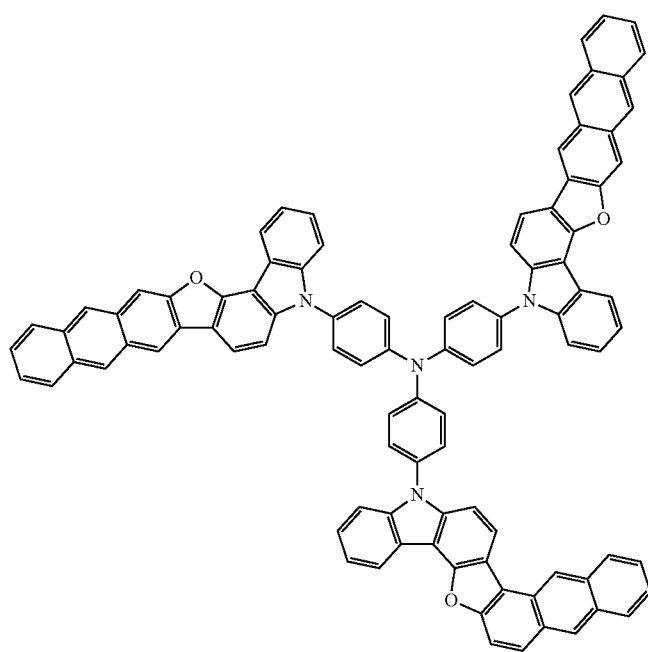
1-10

-continued
1-11
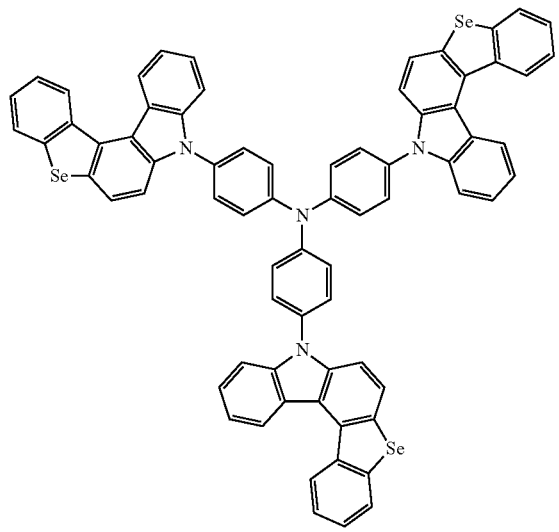
1-12
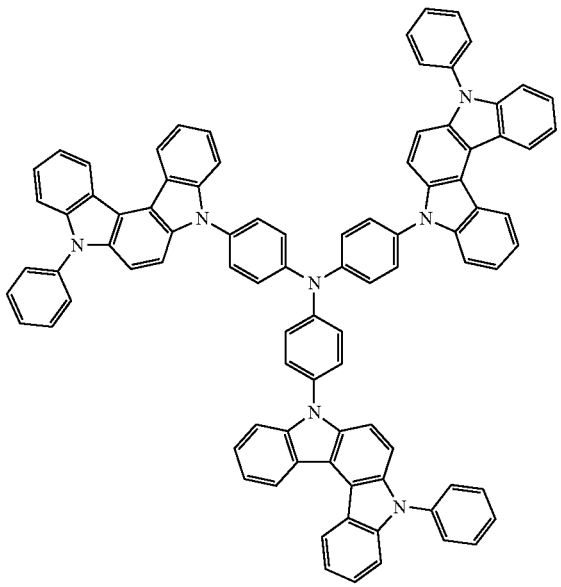
1-13
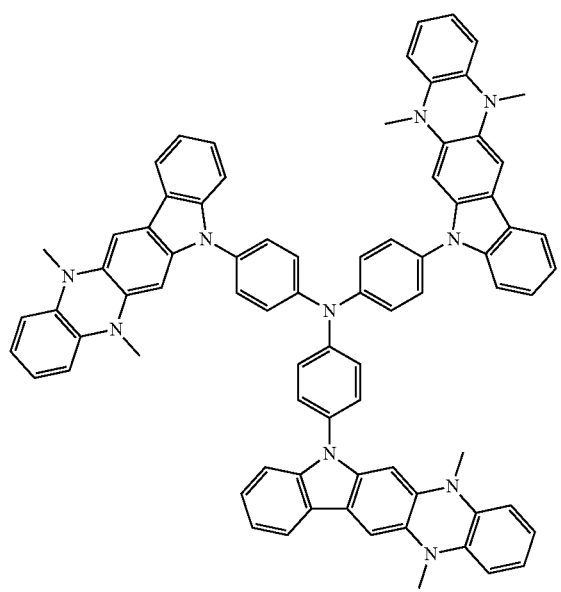
1-14
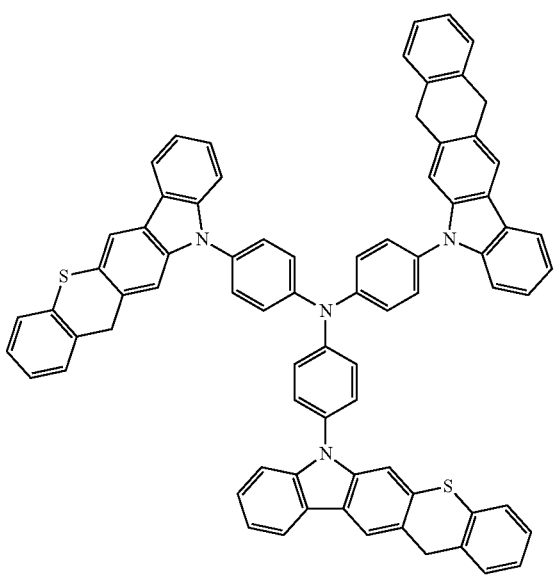

1-15
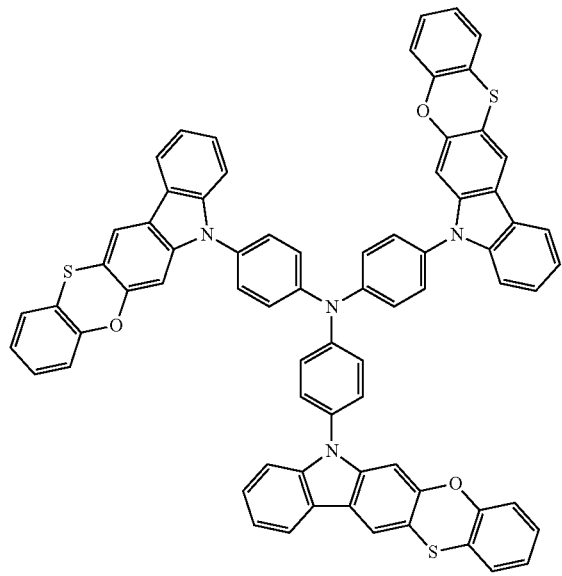
1-16
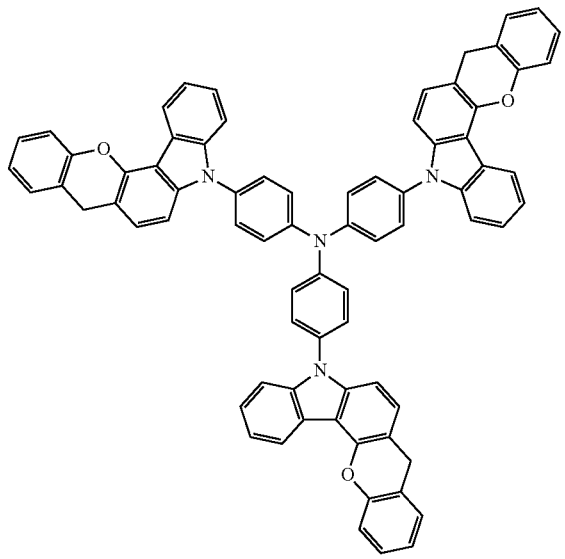
1-17
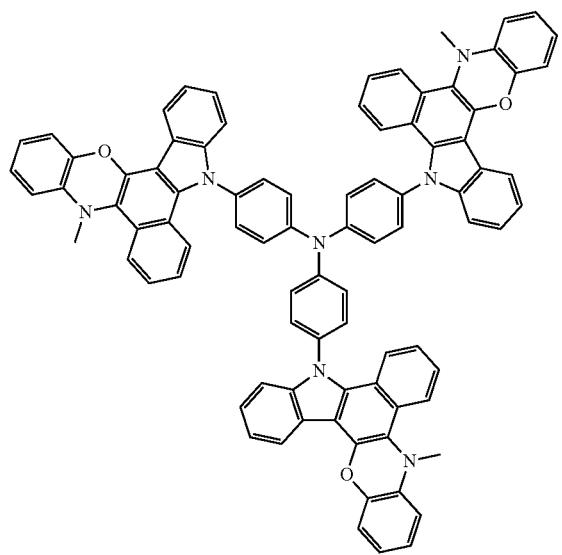
1-18
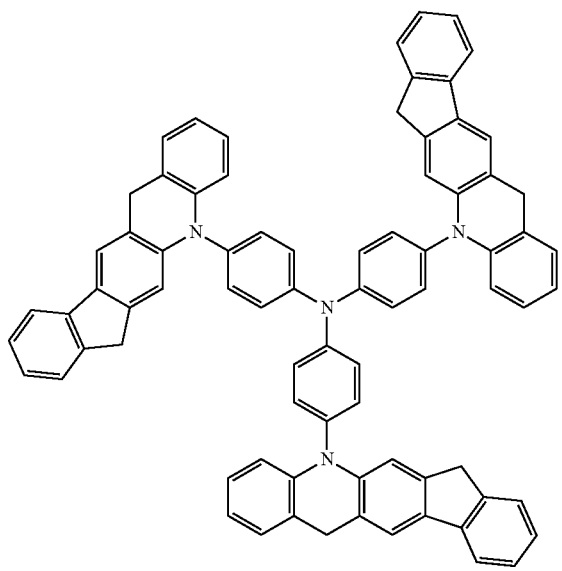

-continued
1-19
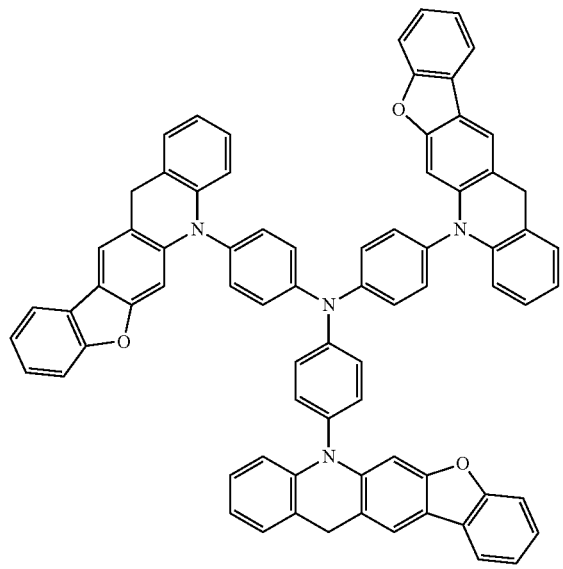
1-20
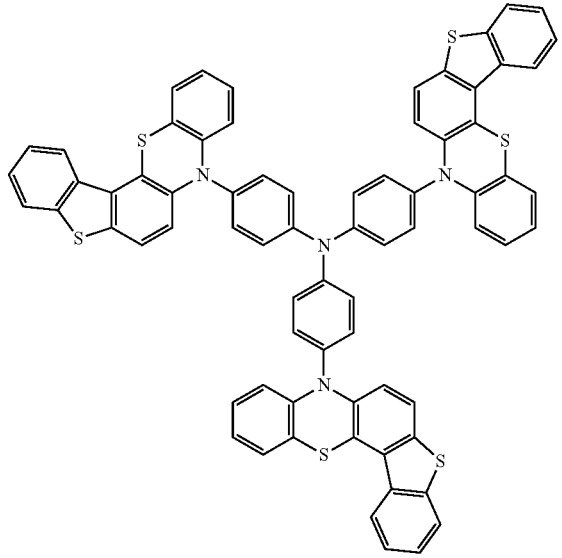
1-21
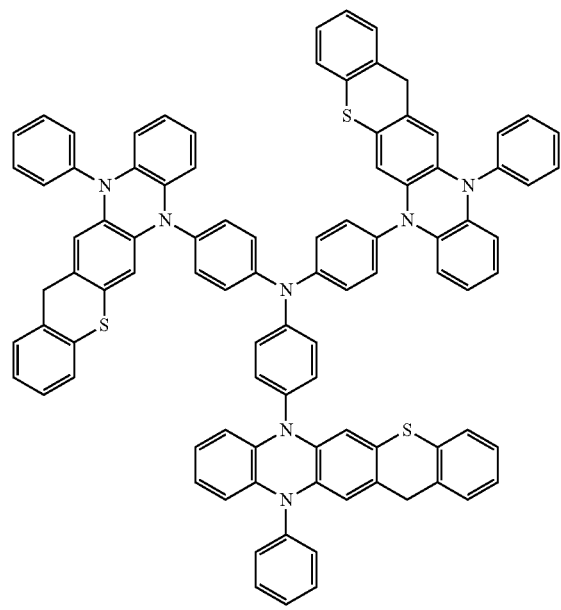
1-22
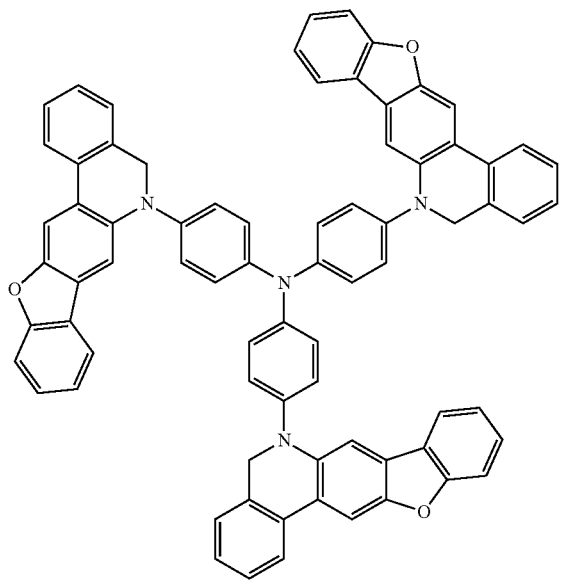

1-23
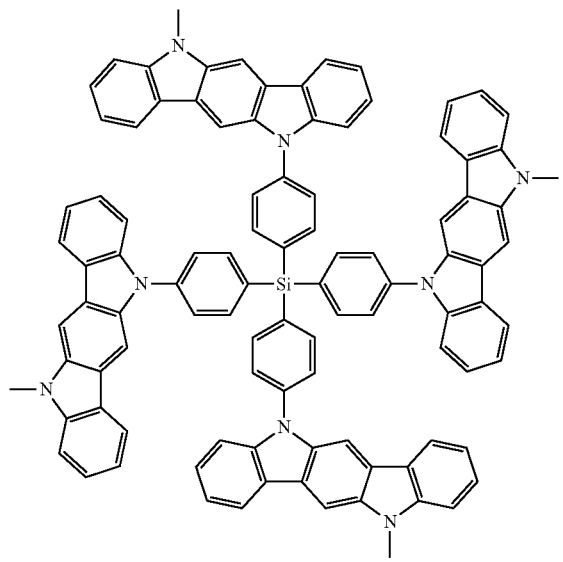
1-24
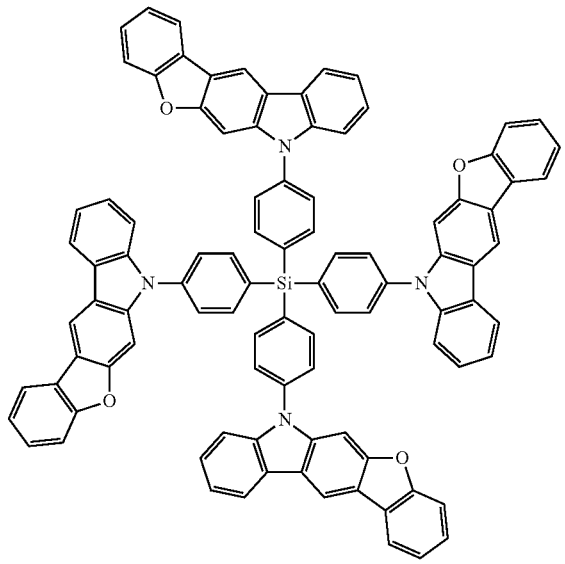
1-25
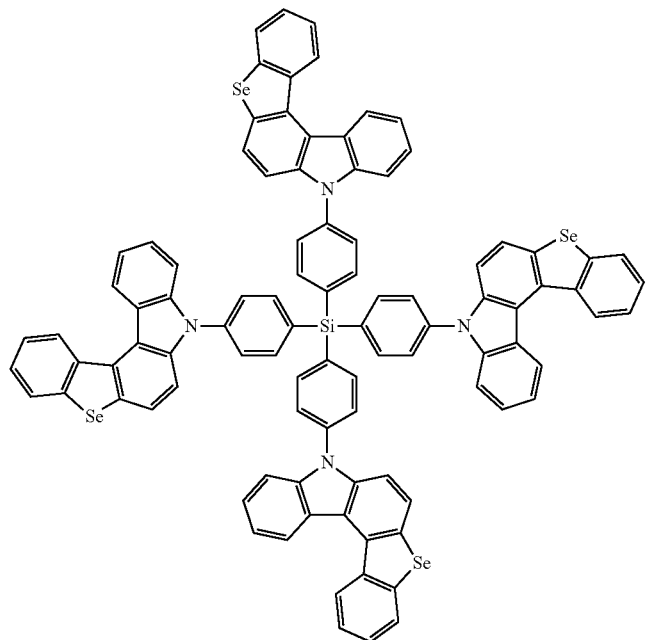

1-26
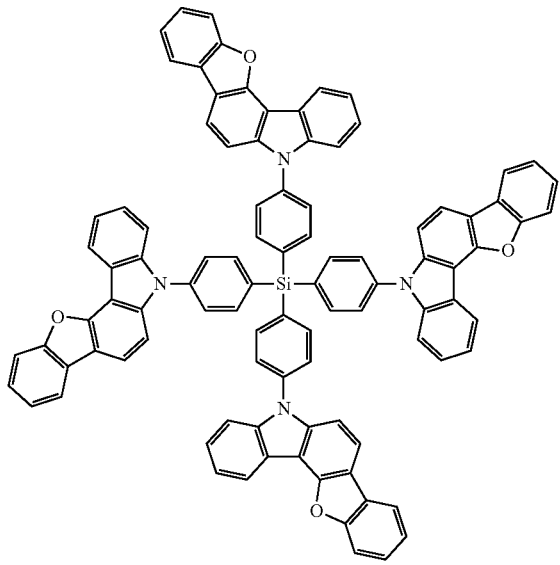
1-27
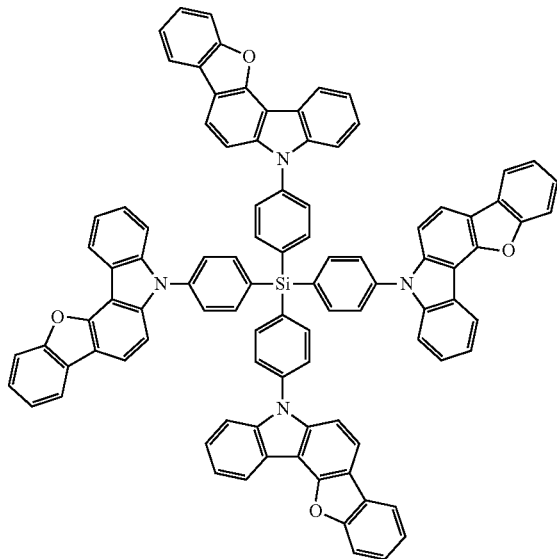
1-28
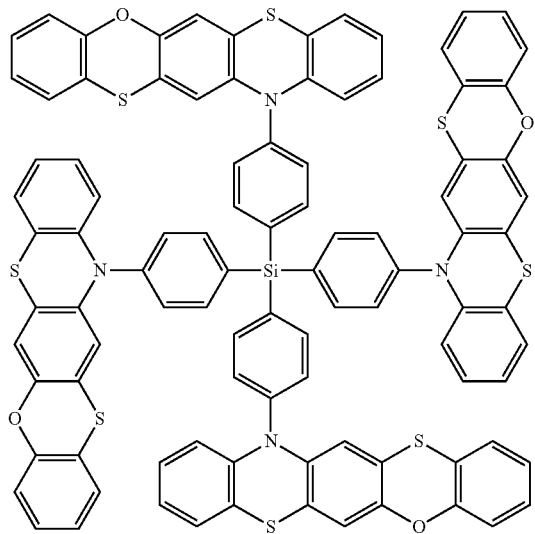

1-29
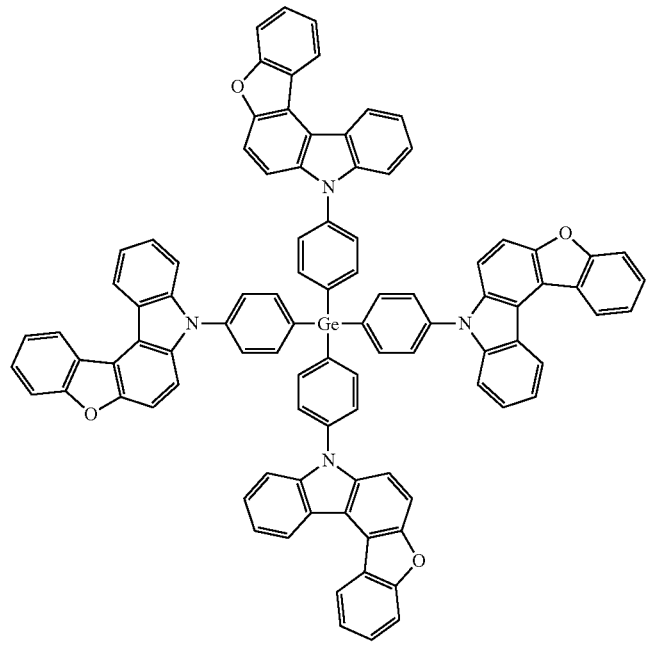
1-30
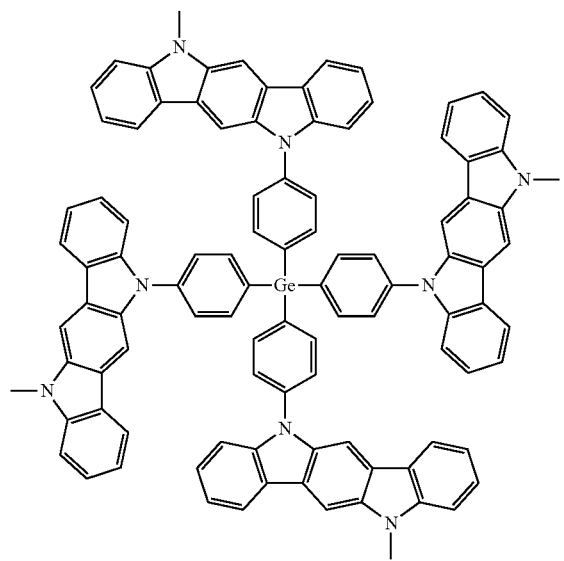
1-31
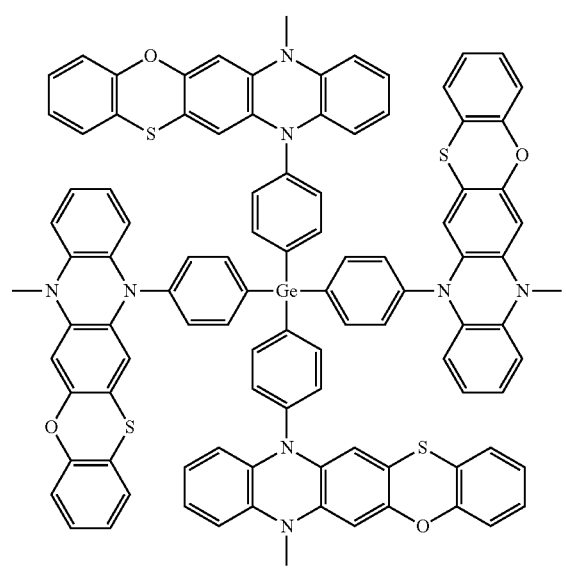

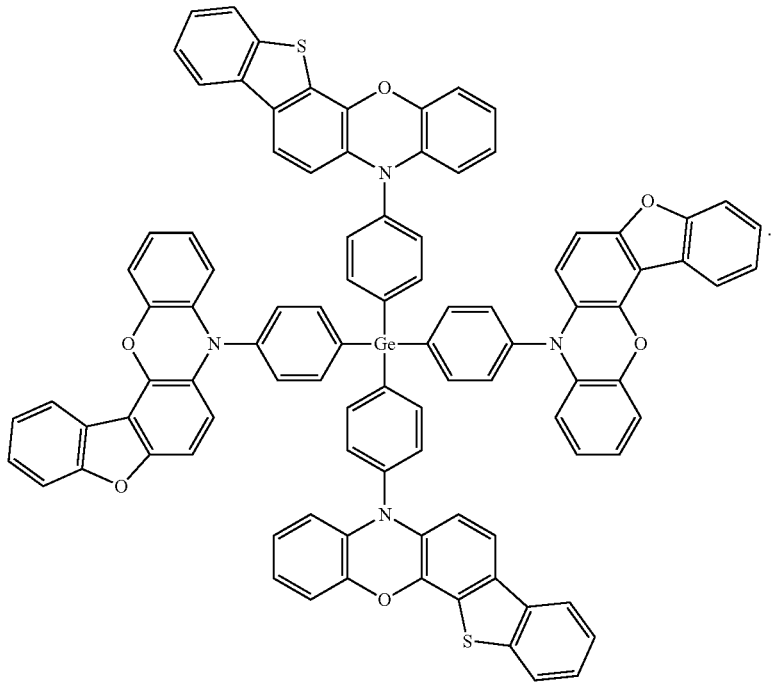
1-32
Preferably, the acceptor host material is a compound with the following structures:
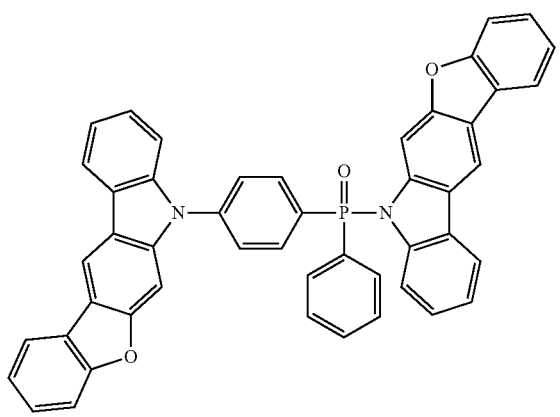
2-1
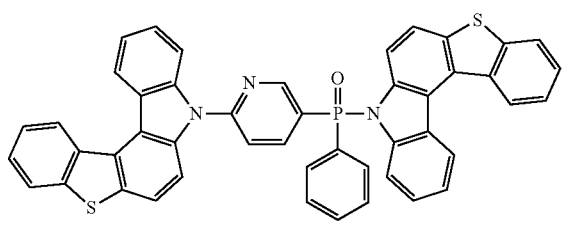
2-2

-continued
2-3
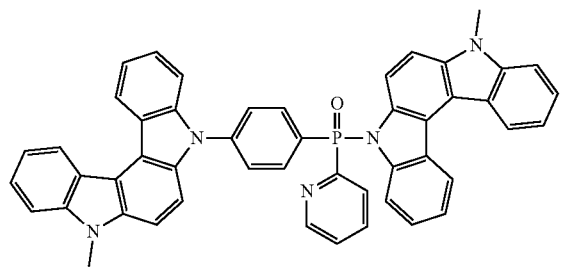
2-4
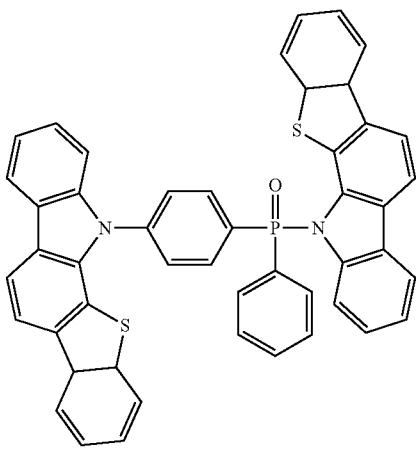
2-5
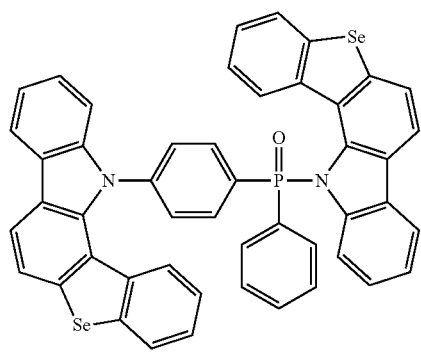
2-6
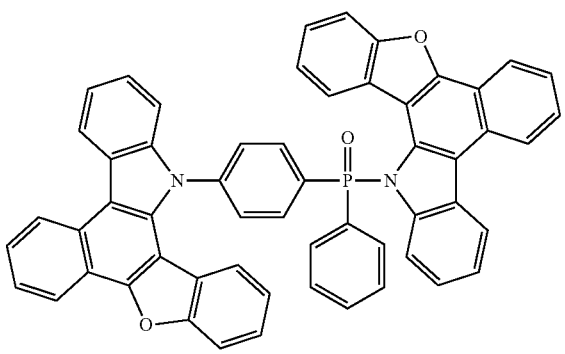
2-7
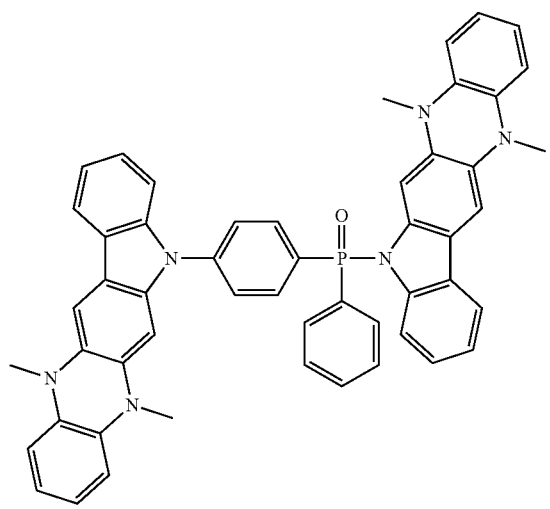
2-8
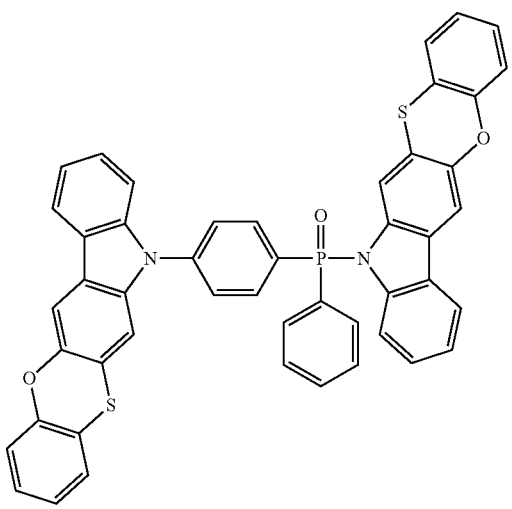

-continued
2-9
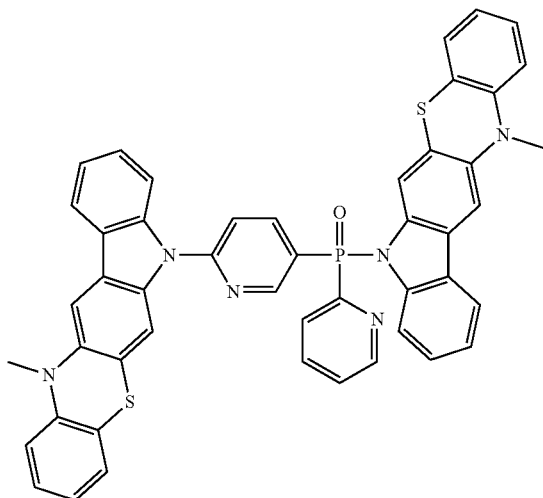
2-10
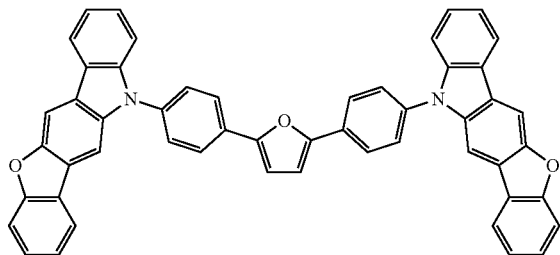
2-11
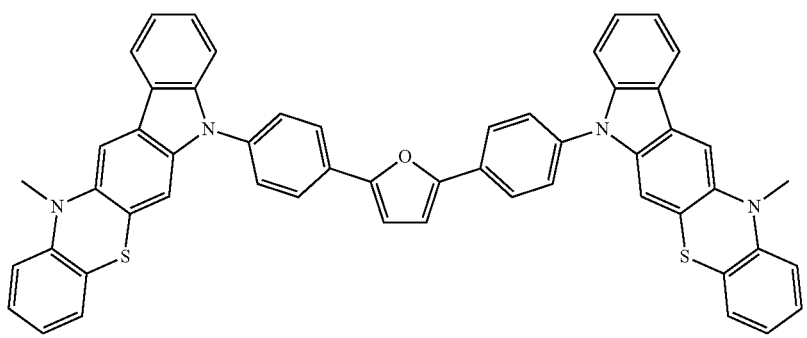
2-12
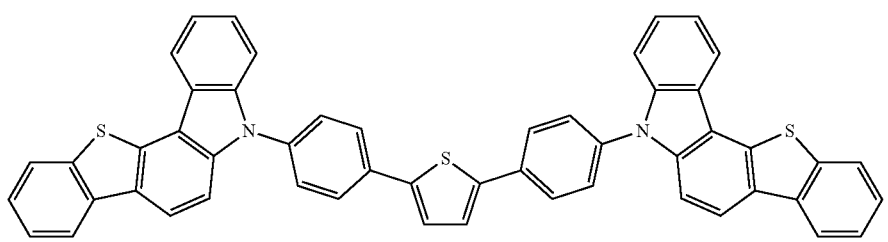
2-13
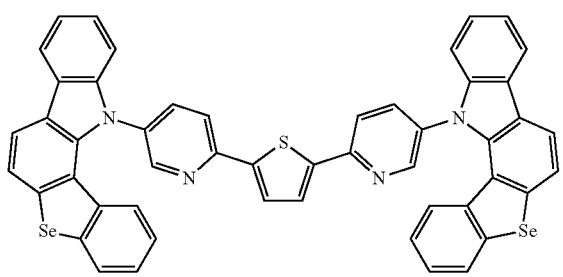
2-14
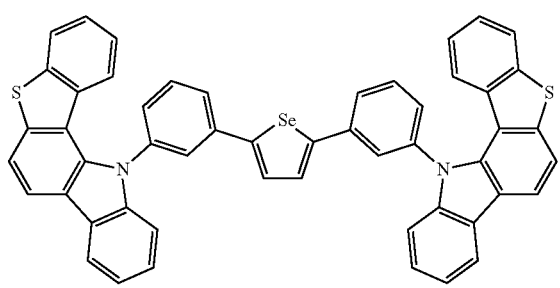

-continued
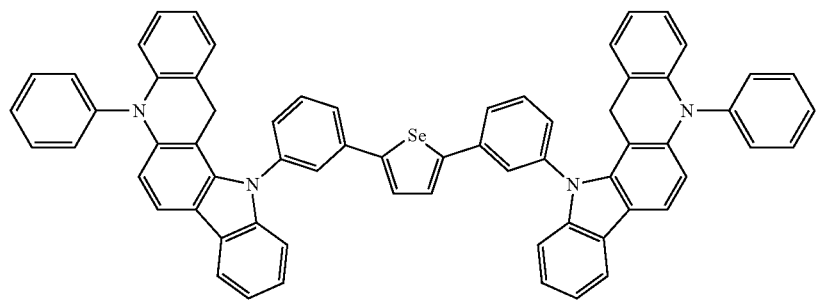
2-15
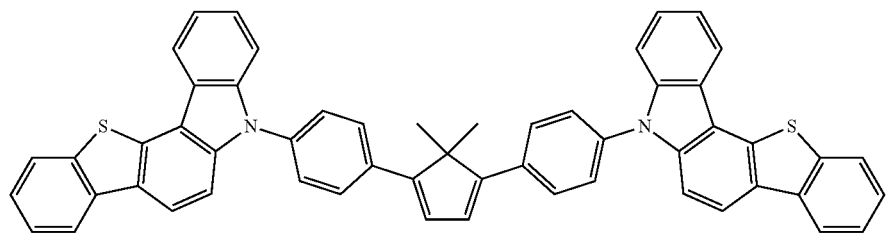
2-16
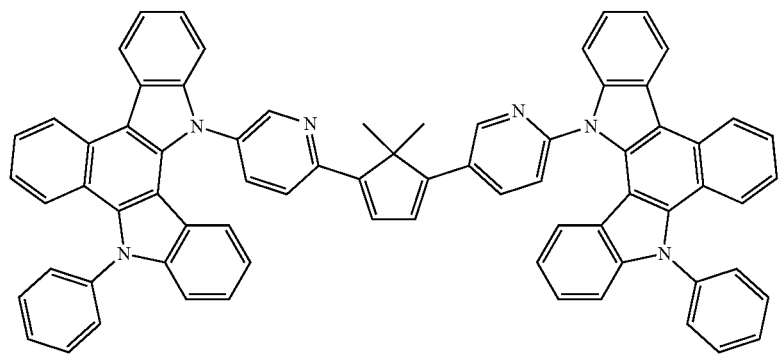
2-17
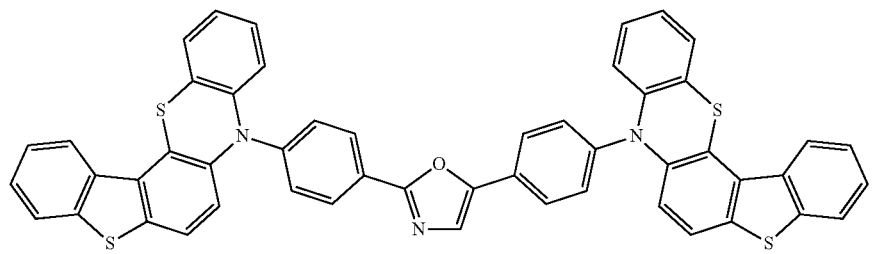
2-18
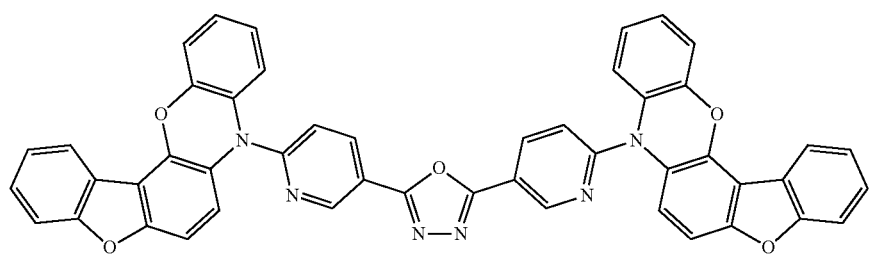
2-19

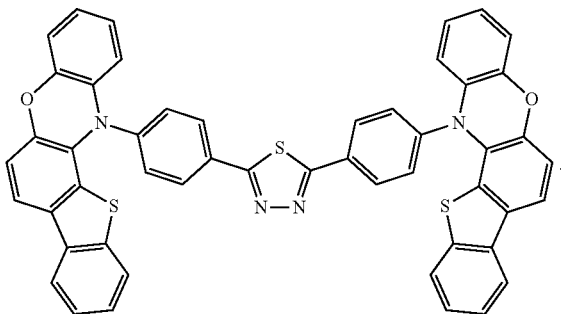

2-20

When a compound which is easy to give electrons and a compound which is easy to receive electrons are respectively used as a donor host material and an acceptor host material, an optimum carrier balance can be achieved by setting the mixing ratio of the two, under the equilibrium condition, the recombination probability of holes and electrons in the light-emitting layer 60 is increased and the luminous efficiency is improved. In an embodiment of the present application, a doping mass ratio of the donor host and the acceptor host is 1:9~9:1.

As a phosphorescent material, in an embodiment of the present application, it is preferably an organometallic complex, and particularly preferably an iridium complex, such as tris (2-p-tolylpyridine) iridium (III) (abbreviation: Ir (mppy)$_3$) or acetylacetonate bis (2-phenylpyridine) iridium (III) (abbreviation: [Ir(ppy)$_2$(acac)]), etc.

Figure 3:
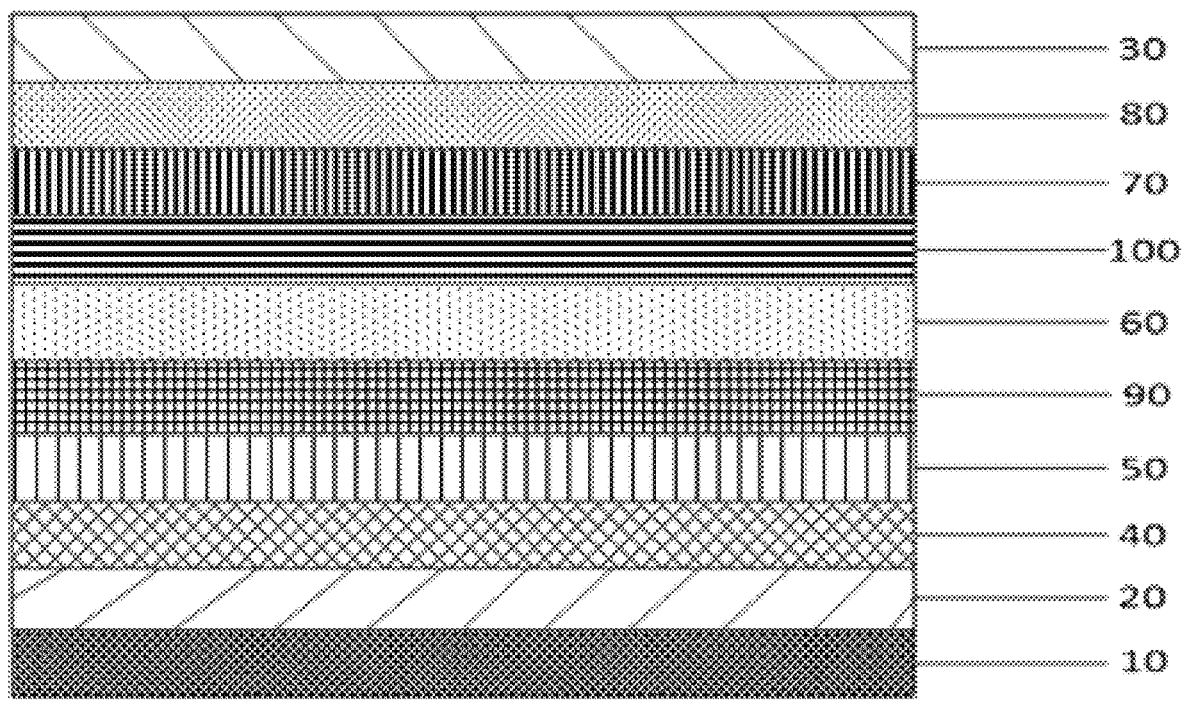
FIG. 3 is a schematic diagram illustrating an organic electroluminescent device according to another embodiment of the present application.

In an embodiment of the present application, as shown in FIG. 3, an optical compensation layer 90 is disposed between the hole transport layer 50 and the light-emitting layer 60. In an embodiment, a material of the optical compensation layer 90 is an electron blocking material with a high hole mobility, and a triplet energy level of the electron blocking material is greater than a triplet energy level of the exciplex produced by the premixed donor host material and acceptor host material. In an embodiment of the present application, the material of the optical compensation layer 90 may be a conventional electron blocking material with a triplet energy level $T_1>2.6$ eV, and the material of the optical compensation layer 90 is not specifically limited by the present application.

In the organic electroluminescent device according to the embodiment of the present application, an electron blocking material with a high triplet energy level is used as an optical compensation layer, so that the color purity and efficiency of the organic electroluminescent device, especially the top-emitting organic electroluminescent green light device, are improved without affecting the driving voltage of the light-emitting device, and the electrons are confined in the region of the light-emitting layer, thus being beneficial to improve the recombination probability of the excitons and further improving the luminous efficiency of the device. In addition, the optical compensation layer in the embodiment is disposed between the light-emitting layer and the hole transport layer, so that the optical compensation layer and the light-emitting layer can be prepared by using the same set of mask plates during the evaporation process, which can avoid the problem of repeated alignment of mask plates caused by disposing the optical compensation layer between the hole injection layer and the hole transport layer in the traditional process, and improve the process precision and the yield rate to a certain extent. This is because there is a certain error in each alignment of the mask plates, so the fewer the number of alignments, the less the error, and the production yield is improved correspondingly.

In another embodiment of the present application, as shown in FIG. 3, a hole blocking layer (HBL) 100 is disposed between the light emitting layer 60 and the electron transport layer 70, and may be formed by a vacuum deposition method, a wet method, a laser transfer method, or the like. As the HBL material, any known hole blocking material, such as an oxadiazole derivative, a triazole derivative or a phenanthroline derivative, can be used. The hole blocking layer can effectively block holes transport, and confine the carrier recombination to the region of the light-emitting layer, thus the luminous efficiency of the device is improved.

The substrate 10 is transparent, and a glass substrate or a flexible substrate made of a compound material such as polyester or polyimide may be used.

The anode layer 20 may be made of an inorganic material or an organic conductive polymer. The inorganic material is generally a metal oxide such as indium tin oxide, zinc oxide, indium zinc oxide, or a metal with a relatively high work function such as gold, copper, silver, among them, indium tin oxide (ITO) is preferred. The organic conductive polymer is preferably one of polythiophene/sodium polyvinylbenzene sulfonate (abbreviation: PEDOT: PSS) and polyaniline (abbreviation: PANI).

The cathode layer 30 is generally made of a metal with a relatively low work function such as lithium, magnesium, calcium, strontium, aluminum or indium, or an alloy of one of them with copper, gold or silver, or an electrode layer formed of the above metal with an alloy or a metal fluoride respectively, such as LiF/Al or Mg:Ag alloy layer/Ag layer.

The hole injection layer 40 is a layer containing a substance with a high hole injecting property, and specifically, metal oxides such as molybdenum oxide, titanium oxide, vanadium oxide, rhenium oxide, ruthenium oxide, chromium oxide, zirconium oxide, silver oxide, tungsten oxide and manganese oxide may be selected. In addition, a phthalocyanine compound such as phthalocyanine (abbreviation: H$_2$Pc) or copper phthalocyanine (II) (abbreviation: CuPc) may be selected.

The hole transport layer 50 is a layer containing a substance with a high hole transporting property, and specifically, aromatic amine compounds such as NPB, TPD, BPAFLP, 4,4'-bis [N-(9,9-dimethylfluoren-2-yl)-N-phenylamino] biphenyl (abbreviation: DFLDPBi) and 4,4'-bis [N-(spiro-9,9'-bifluoren-2-yl)-N-phenylamino] biphenyl (abbreviation: BSPB) may be selected. Carbazole derivatives such as CBP, CzPA and PCzPA, or anthracene derivatives such as t-BuDNA, DNA and DPAnth, may also be selected.

The electron transport layer 70 is a layer containing a substance with a high electron transporting property, and specifically, metal complexes such as $Alq_3$, tris (4-methyl-8-hydroxyquinoline) aluminum (abbreviation: $Almq_3$), bis (10-hydroxybenzo [h] quinoline) beryllium (abbreviation: $BeBq_2$), BAlq, $Zn(BOX)_2$ and bis [2-(2-hydroxyphenyl) benzothiazole] zinc (abbreviation: $Zn(BTZ)_2$) may be selected. Heteroaromatic compounds such as 2-(4-biphenyl)-5-(4-tert-butylphenyl)-1,3,4-oxadiazole (abbreviation: PBD), 1,3-bis [5-(p-tert-butylphenyl)-1,3,4-oxadiazol-2-yl] benzene (abbreviation: OXD-7), 3-(4-tert-butylphenyl)-4-phenyl-5-(4-biphenyl)-1,2,4-triazole (abbreviation: TAZ), 3-(4-tert-butylphenyl)-4-(4-ethylphenyl)-5-(4-biphenyl)-1,2,4-triazole (abbreviation: p-EtTAZ) and red phenanthroline (abbreviation: BPhen) may also be selected.

The electron injection layer 80 is a layer containing a substance with a high electron injecting property, and alkali metals, alkaline earth metals and compounds thereof may be selected, such as lithium, cesium, calcium, lithium fluoride, cesium fluoride, calcium fluoride, erbium fluoride or lithium oxide, etc. The organic electroluminescent device provided by the present application will be further illustrated through specific embodiments. However, the present application is not limited by the following embodiments.

Embodiment 1

A host material of a light-emitting layer of an organic electroluminescent device in the present embodiment is formed by premixing a donor host material and an acceptor host material with different mass ratios, and the structure of the device is shown in FIG. 3. The host material of the light-emitting layer 60 is an exciplex (wherein a donor host material is 1-2, a acceptor host material is 2-3, and the exciplex is formed of the donor host material 1-2 and the acceptor host material 2-3 through a single-source evaporation method), a phosphorescent material doped in the host material is $Ir(mppy)_3$, a optical compensation layer 90 is disposed between a hole transport layer 50 and a light-emitting layer 60, and the material of the optical compensation layer 90 is an electron blocking material mCBP with a high mobility.

The device structure of the present embodiment is as follows:

ITO (20 nm)/hole injection layer (HATCN, 10 nm)/hole transport layer (TCTA, 80 nm)/optical compensation layer (mCBP, 70 nm)/donor host material (1-2, 10 nm): acceptor host material (2-3): 10% phosphorescent material Ir $(mppy)_3$/electron transport layer (TPBi, 30 nm)/electron injection layer (Bphen, 10 nm)/Mg:Ag (1:4, 1 nm)/Ag (15 nm)

Comparative Example 1

The structure of the device is as follows:
ITO (20 nm)/hole injection layer (HATCN, 10 nm)/optical compensation layer (mCBP, 150 nm)/mCBP (20 nm): 10% phosphorescent material $Ir(mppy)_3$/electron transport layer (TPBi, 30 nm)/electron injection layer (Bphen, 10 nm)/Mg:Ag (1:4, 1 nm)/Ag (15 nm)

The properties of the organic electroluminescent devices of the above embodiment 1 and comparative example 1 are shown in Table 1 below:

TABLE 1

| Device | Host materials in the light-emitting layer (mass ratio) | Voltage (V) | Current efficiency (cd/A) | Brightness (cd/m$^2$) | Lifetime (T97@10 Knit) h | CIE-x | CIE-y |
|---|---|---|---|---|---|---|---|
| Embodiment 1 | Donor host material (1-2):Acceptor host material (2-3) = 1:1 | 4.3 | 99 | 5000 | 1290 | 0.26 | 0.70 |
| | Donor host material (1-2):Acceptor host material (2-3) = 1:2 | 4.0 | 101 | 5000 | 1275 | 0.24 | 0.72 |
| | Donor host material (1-2):Acceptor host material (2-3) = 2:1 | 3.9 | 105 | 5000 | 1280 | 0.25 | 0.71 |
| | Donor host material (1-2):Acceptor host material (2-3) = 2:3 | 3.8 | 110 | 5000 | 1320 | 0.24 | 0.72 |
| | Donor host material (1-2):Acceptor host material (2-3) = 3:2 | 3.9 | 106 | 5000 | 1300 | 0.24 | 0.72 |
| Comparative Example 1 | mCBP | 4.6 | 90 | 5000 | 620 | 0.26 | 0.70 |

It can be seen from the data in Table 1, the current efficiency and T97 lifetime of the host material premixed by the donor host and the acceptor host are higher than those without premixing (comparative example 1), wherein when the mass ratio of the donor host material (1-2) and the acceptor host material (2-3) is 2:3, the device performance is the best, the current efficiency is improved by 22% compared with the comparative example 1, T97 lifetime is more than doubled, and the device lifetime T97 in embodiment 1 can reach more than 1000 hours.

Embodiment 2

An organic electroluminescent device is prepared with reference to embodiment 1, wherein the donor host material is the above-mentioned donor host material 1-24 of the present application, the acceptor host material is the above-mentioned acceptor host material 2-10 of the present application, and the mass ratio of the two is 2:3. The performance of the device is shown in Table 2.

Embodiment 3

An organic electroluminescent device is prepared with reference to embodiment 1, wherein the donor host material is the above-mentioned donor host material 1-30 of the present application, the acceptor host material is the above-mentioned acceptor host material 2-16 of the present application, and the mass ratio of the two is 2:3. The performance of the device is shown in Table 2.

TABLE 2

| Device | Host materials in the light-emitting layer (mass ratio) | Voltage (V) | Current Efficiency (cd/A) | Brightness (cd/m$^2$) | Lifetime (T97@10 Knit) h | CIE-x | CIE-y |
|---|---|---|---|---|---|---|---|
| Embodiment 2 | Donor host material (1-24):Acceptor host material (2-10) = 2:3 | 3.8 | 108 | 5000 | 1380 | 0.24 | 0.72 |
| Embodiment 3 | Donor host material (1-30):Acceptor host material (2-16) = 2:3 | 3.8 | 112 | 5000 | 1340 | 0.25 | 0.71 |

The embodiments of the present application further provide a manufacturing method for an organic electroluminescent device. The manufacturing method includes: disposing an anode on a substrate; disposing a light-emitting layer on the anode, wherein a host material of the light-emitting layer is formed by premixing a donor host material and an acceptor host material, the donor host material and the acceptor host material are co-evaporated in a same evaporation source to form an exciplex, and the host material is doped with a guest material; and disposing a cathode on the light-emitting layer.

In the embodiments of the present application, the problem of the serious roll-off drop under high brightness is effectively solved, the stability of the device is further improved, at the same time, the doping concentration of the guest material is reduced, and thus the product cost is reduced.

In embodiments of the present application, the manufacturing method further includes: sequentially stacking a hole injection layer and a hole transport layer between the anode and the light-emitting layer; and disposing an optical compensation layer between the hole transport layer and the light-emitting layer. Specifically, the hole injection layer is disposed on the anode, the hole transport layer is disposed on the hole injection layer, and further, the optical compensation layer is disposed on the hole transport layer, and the optical compensation layer is located under the light-emitting layer.

In the embodiments of the present application, the anode, the hole injection layer, the hole transport layer, the optical compensation layer, the light-emitting layer, the cathode, and the like may be sequentially stacked on the substrate through a conventional evaporation or coating process.

The above descriptions are merely preferred embodiments of the present application, and are not intended to limit the present application. Any modification, equivalent substitution, etc. made within the spirit and principles of the present application shall be included in the protection scope of the present application.

INDUSTRIAL APPLICABILITY

In an organic electroluminescent device and a manufacturing method thereof according to the present application, a host material of a light-emitting layer is co-evaporated by a donor host material and a acceptor host material in a same evaporation source to form an exciplex, thus not only the balance between the electron and hole carriers can be facilitated, the lifetime and efficiency of the device are improved, but also the difficulty of process operation is reduced and the yield of mass production is improved by the single-source evaporation.

What is claimed is:

1. An organic electroluminescent device, comprising:
an anode,
a cathode, and
a light-emitting layer disposed between the anode and the cathode, a host material of the light-emitting layer being formed by premixing a donor host material and a acceptor host material, the donor host material and the acceptor host material being co-evaporated in a same evaporation source to form an exciplex, the host material being doped with a guest material,
wherein a triplet energy level of the donor host is greater than a singlet energy level of the exciplex, an energy gap between the triplet energy level of the donor host and the singlet energy level of the exciplex is greater than or equal to 0.2 eV; and an absolute value of HOMO energy level of the donor host is less than or equal to 5.3 eV;
a triplet energy level of the acceptor host is greater than a singlet energy level of the exciplex, an energy gap between the triplet energy level of the acceptor host and the singlet energy level of the exciplex is greater than 0.2 eV; and an absolute value of LUMO energy level of the acceptor host is greater than 2.0 eV; and
glass transition temperatures of the donor host and the acceptor host are greater than 100° C.

2. The organic electroluminescent device according to claim 1, further comprising a hole injection layer and a hole transport layer sequentially stacked on the anode, and an optical compensation layer disposed between the hole transport layer and the light-emitting layer.

3. The organic electroluminescent device according to claim 2, wherein the optical compensation layer is made of an electron blocking material, and a triplet energy level of the electron blocking material is greater than a triplet energy level of the exciplex.

4. The organic electroluminescent device according to claim 1, wherein evaporation temperatures of the donor host and the acceptor host are respectively 150° C.~500° C.

5. The organic electroluminescent device according to claim 1, wherein an absolute value of a difference between evaporation temperatures of the donor host and the acceptor host is less than 30° C.

6. The organic electroluminescent device according to claim 1, wherein a doping mass ratio of the donor host and the acceptor host is 1:9~9:1.

7. The organic electroluminescent device according to claim 1, wherein a molecular formula of the donor host material is:

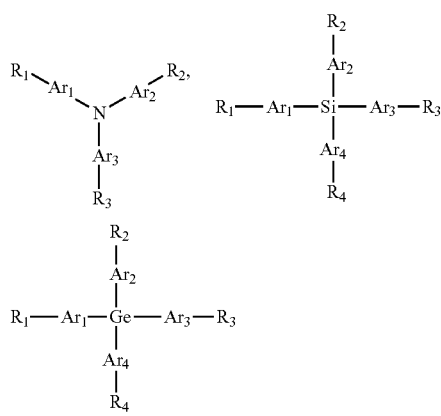

wherein $Ar_1$, $Ar_2$, $Ar_3$ and $Ar_4$ substituents are same or different, and are independently selected from an arylene group or a heteroarylene group; and structures of $R_1$, $R_2$, $R_3$ and $R_4$ are

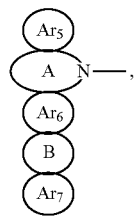

wherein $Ar_5$, A, $Ar_6$, B and $Ar_7$ are connected in a fused ring manner, sharing two atoms, $Ar_5$, $Ar_6$ and $Ar_7$ are the same or different, are independently selected from a benzene ring, a substituted benzene ring, a naphthalene ring, a substituted naphthalene ring, an anthracene ring or a substituted anthracene ring, A is a five-membered heterocyclic ring or a six-membered heterocyclic ring containing nitrogen atoms, and B is a five-membered ring, a five-membered heterocyclic ring, a six-membered ring or a six-membered heterocyclic ring; and/or, a molecular formula of the acceptor host material is:

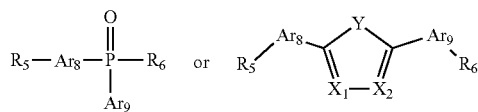

wherein $X_1$ and $X_2$ are same or different, and are —CH— or —N— respectively;

Y is —O—, —S—, —Se—, —C(CH₃)₂—, —C(C₆H₅)₂— or —C(9-fluorenyl)-;

$Ar_8$ and $Ar_9$ substituents are the same or different, and are independently selected from an arylene group or a heteroarylene group; and structures of $R_5$ and $R_6$ are

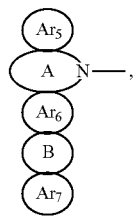

wherein $Ar_{10}$, C ring, $Ar_{11}$, D ring and $Ar_{12}$ are connected in a fused ring manner, sharing two atoms, and $Ar_{10}$, $Ar_{11}$ and $Ar_{12}$ are the same or different, and are independently selected from a benzene ring, a substituted benzene ring, a naphthalene ring or a substituted naphthalene ring, C ring is a five-membered heterocyclic ring or a six-membered heterocyclic ring containing nitrogen atoms, and D ring is a five-membered ring, a five-membered heterocyclic ring, a six-membered ring or a six-membered heterocyclic ring.

8. The organic electroluminescent device according to claim 7, wherein the $R_1$, $R_2$, $R_3$, $R_4$, $R_5$ and $R_6$ are independently selected from any one of the following molecular structures:

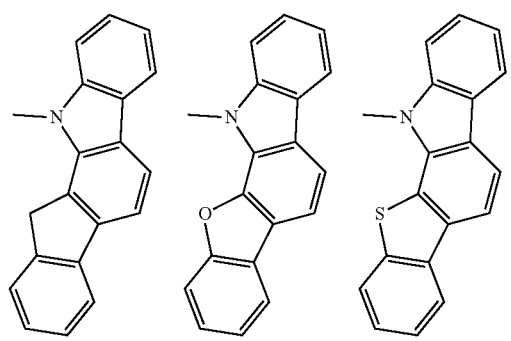

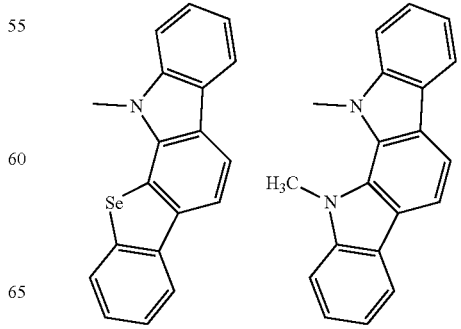

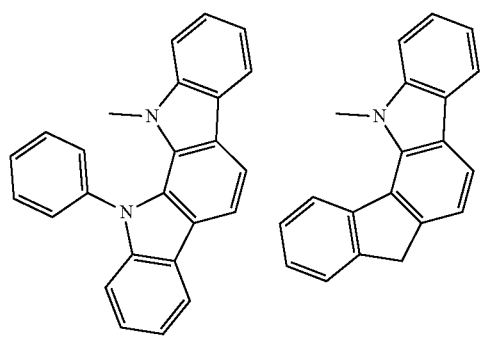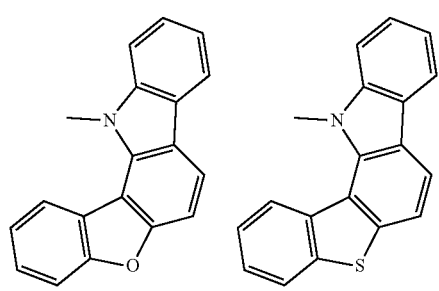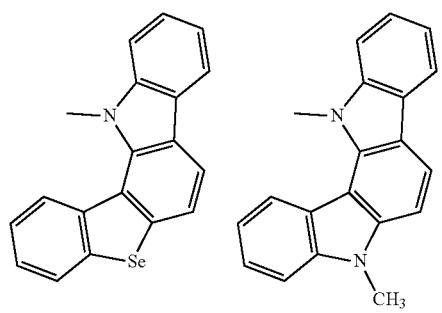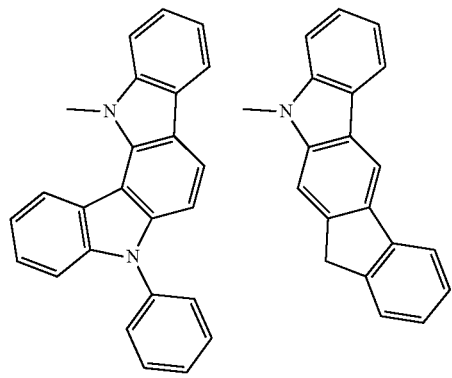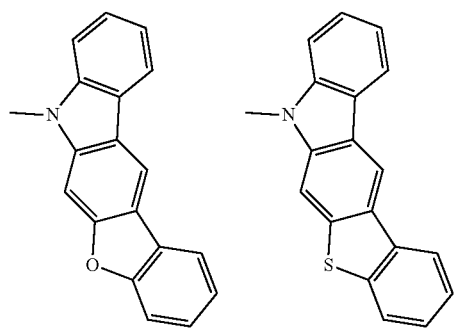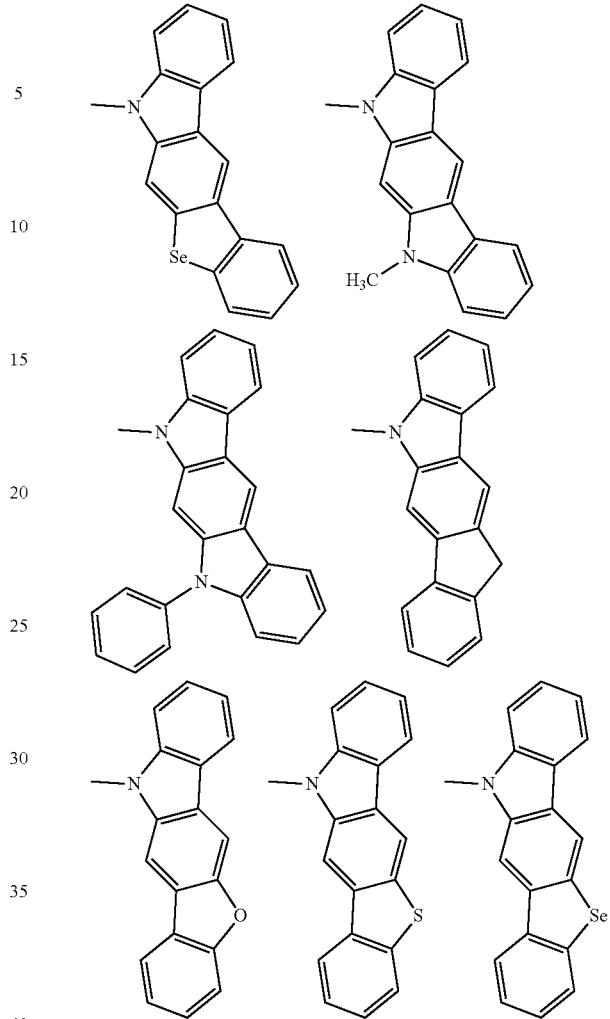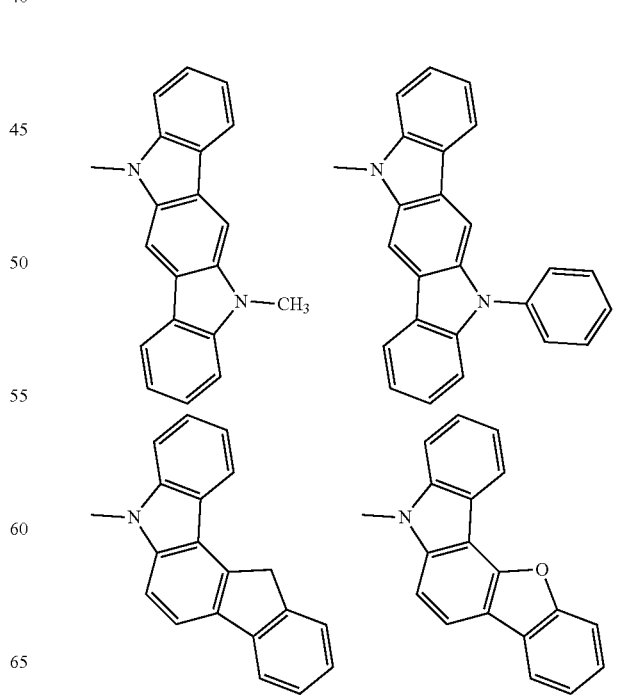

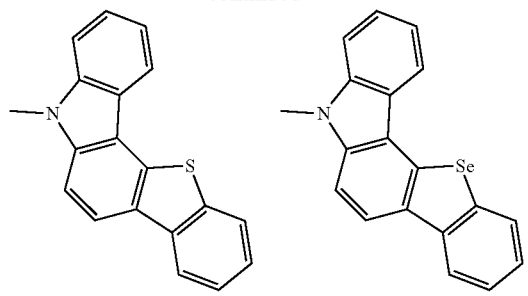
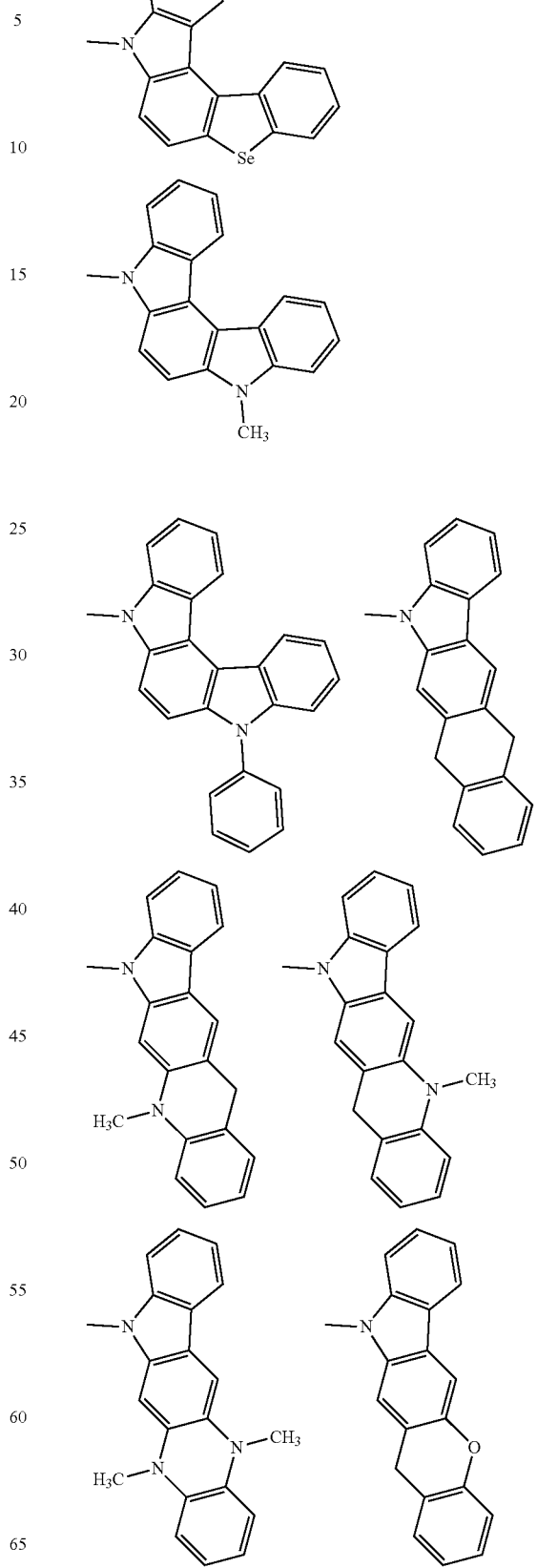

-continued
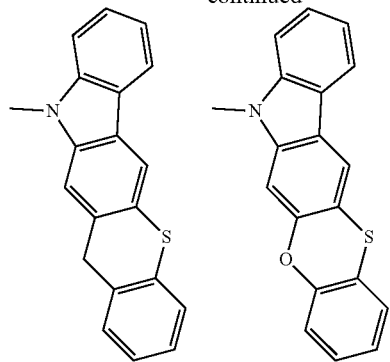
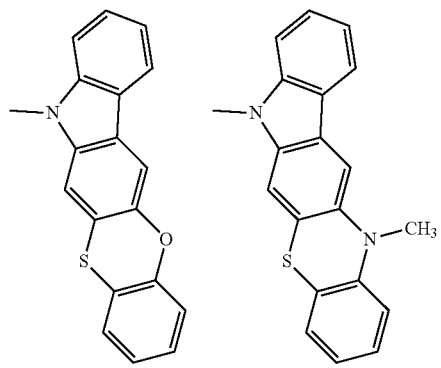
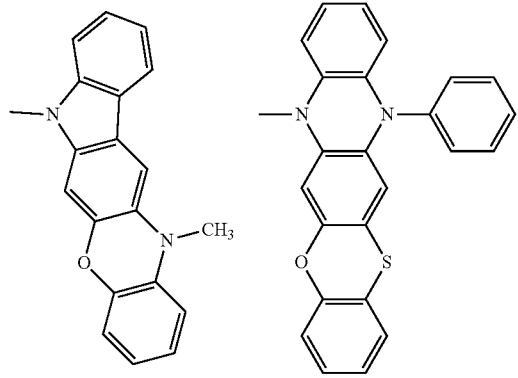
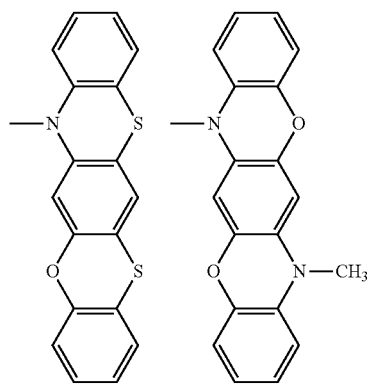
-continued
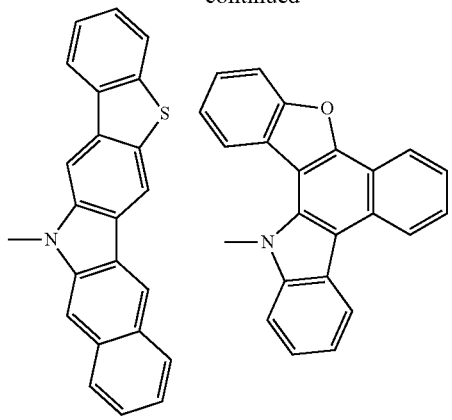
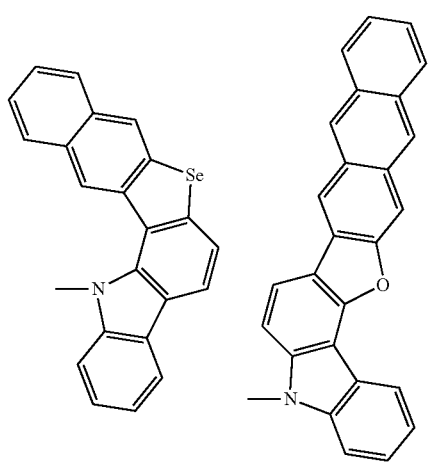
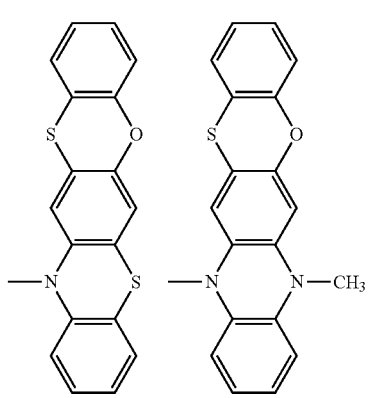
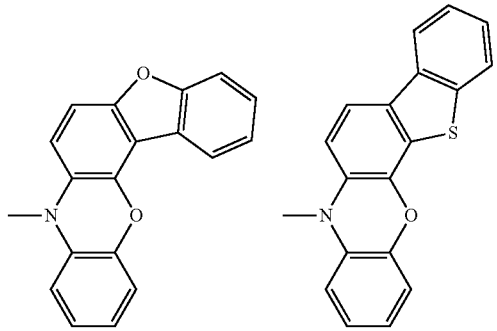

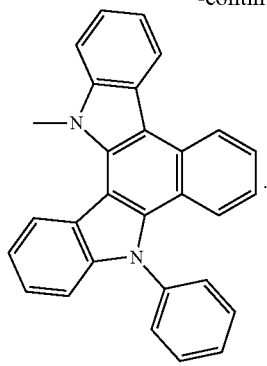
9. The organic electroluminescent device according to claim 7, wherein the donor host material is a compound with the following structures:
1-1
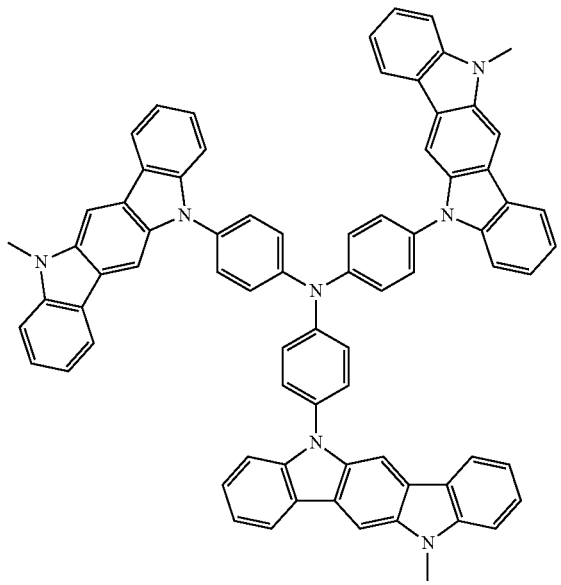
1-2
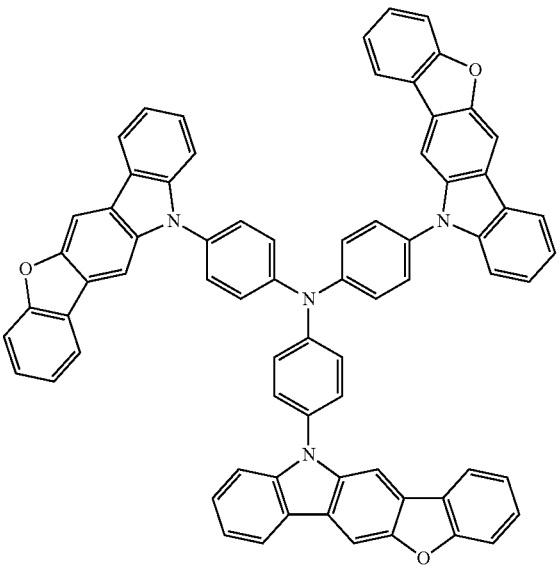
1-3
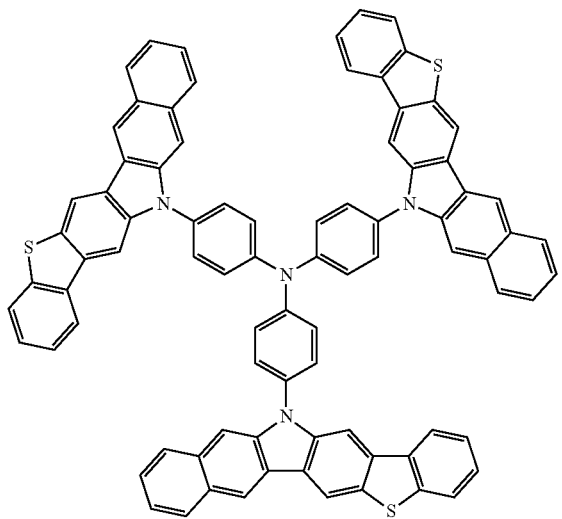
1-4
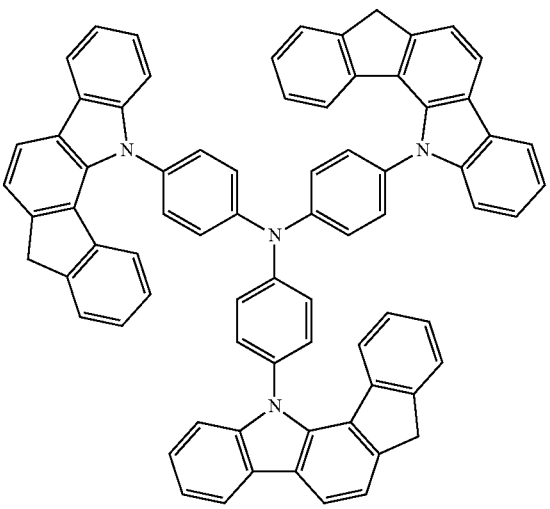

-continued
1-5
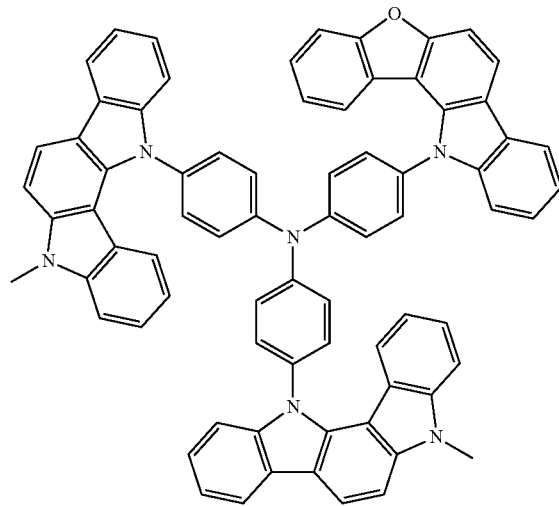
1-6
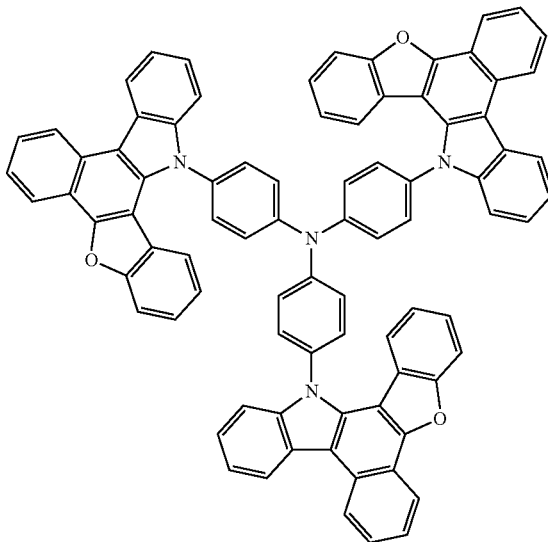
1-7
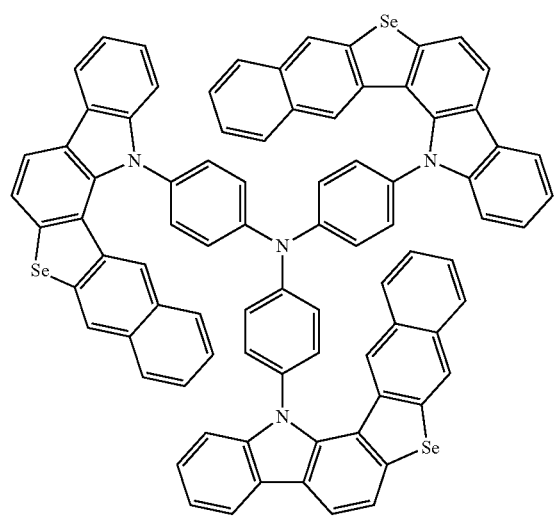
1-8
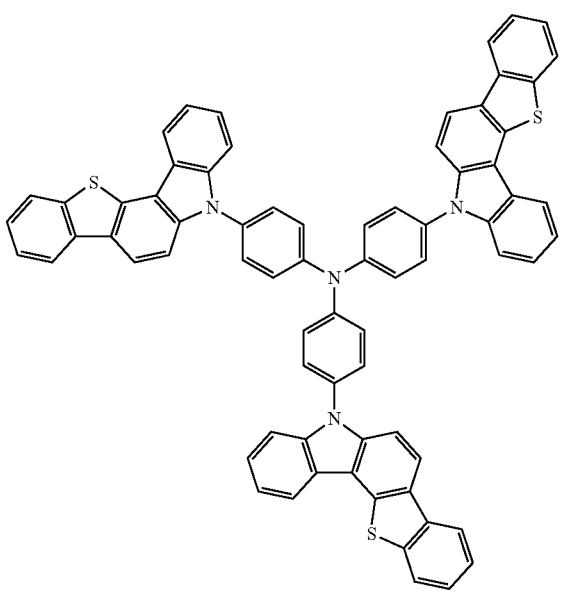

-continued
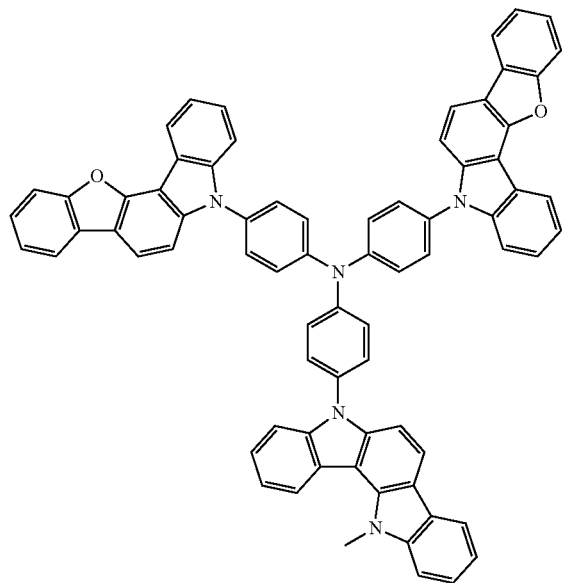
1-9
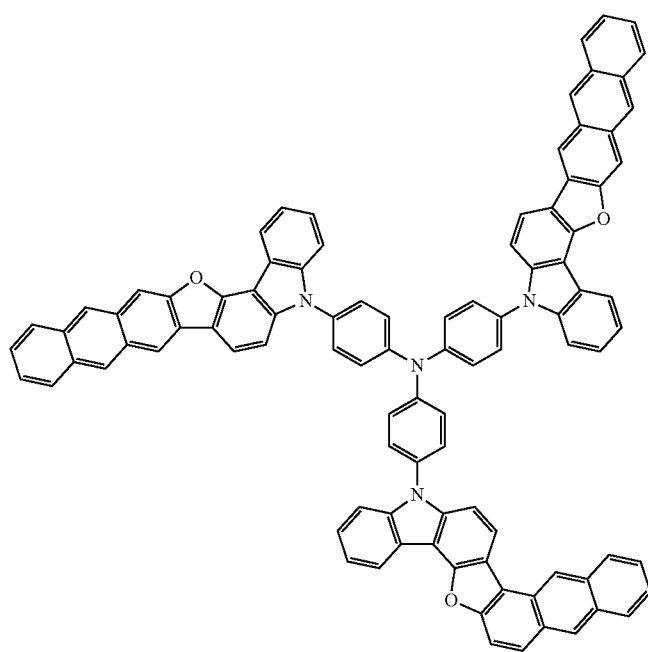
1-10

1-11
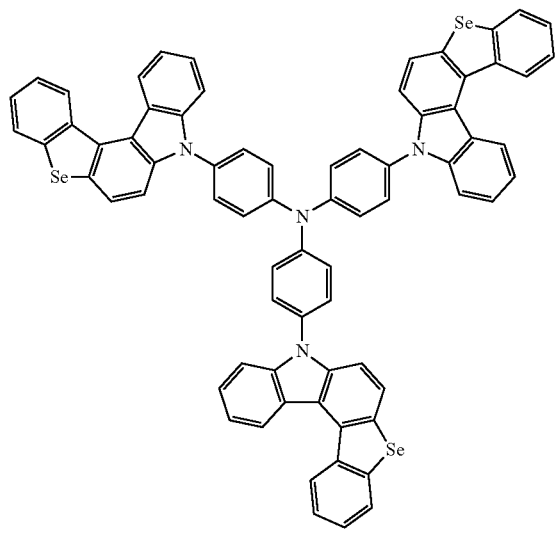
1-12
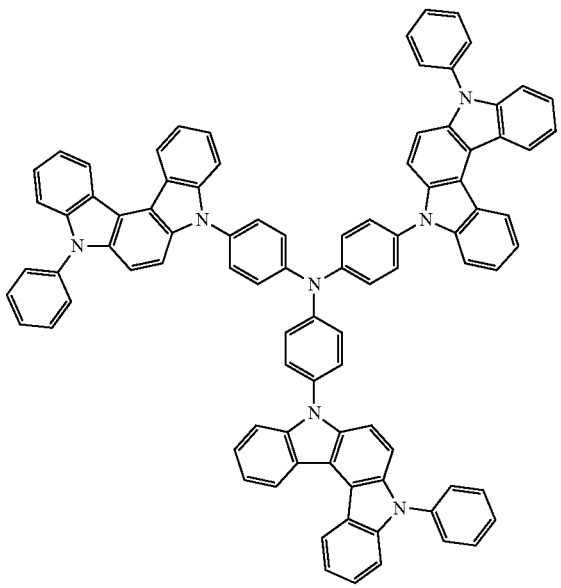
1-13
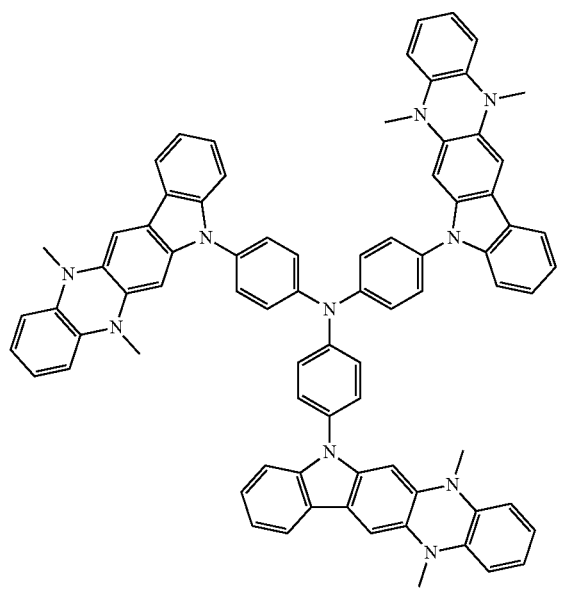
1-14
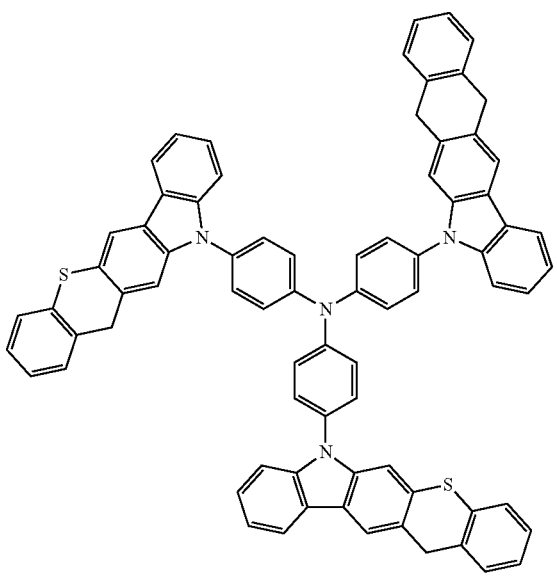

1-15
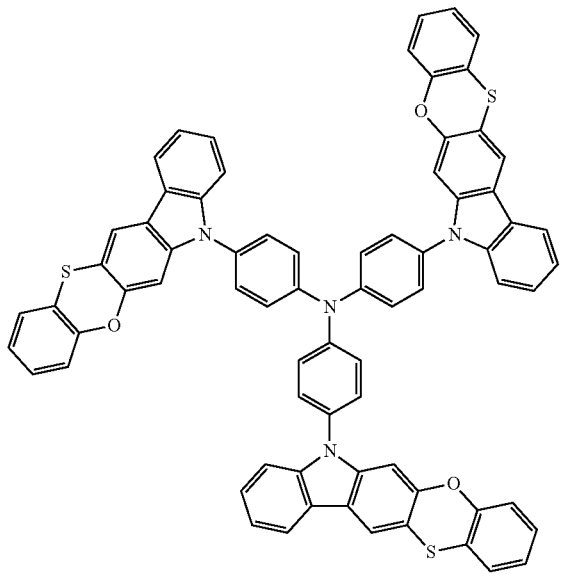
1-16
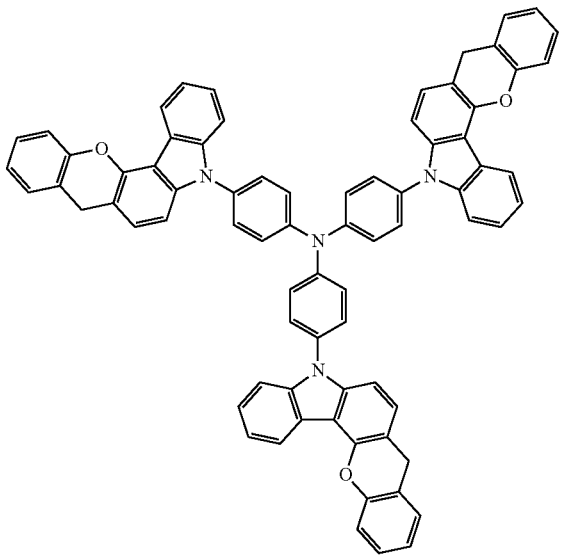
1-17
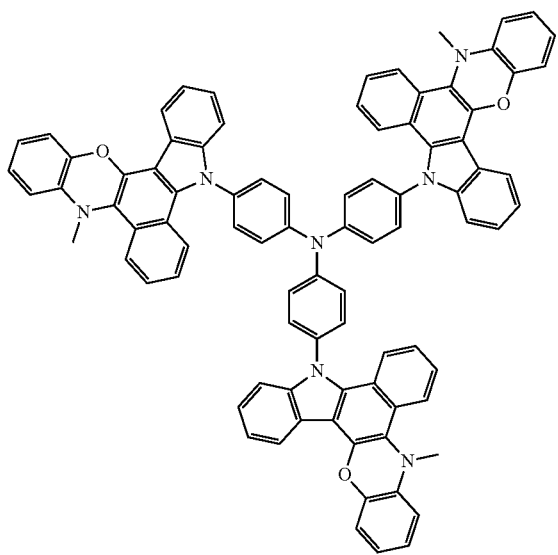
1-18
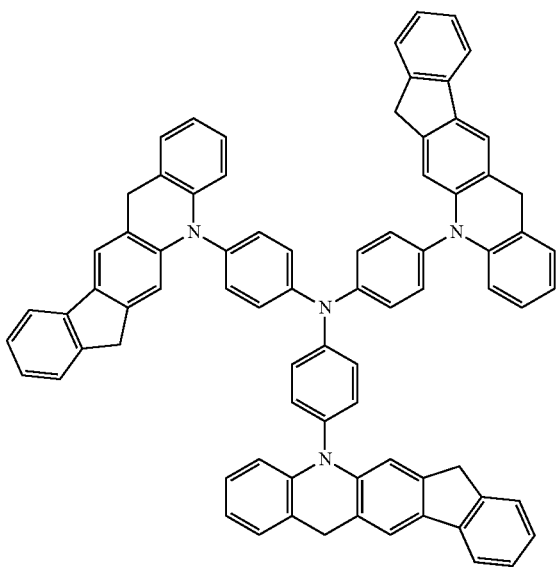

1-19
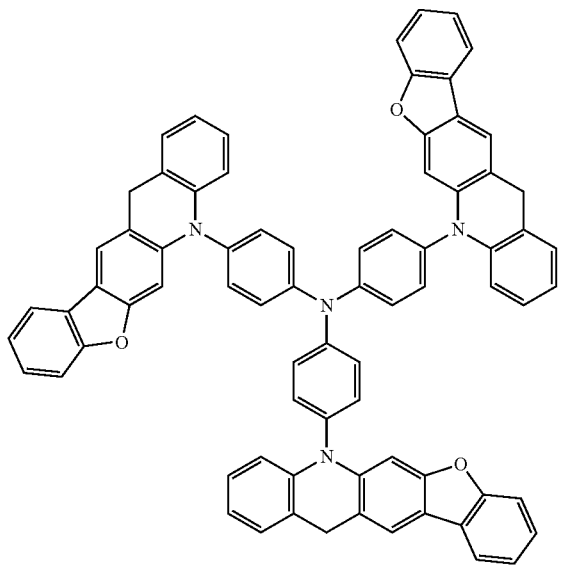
1-20
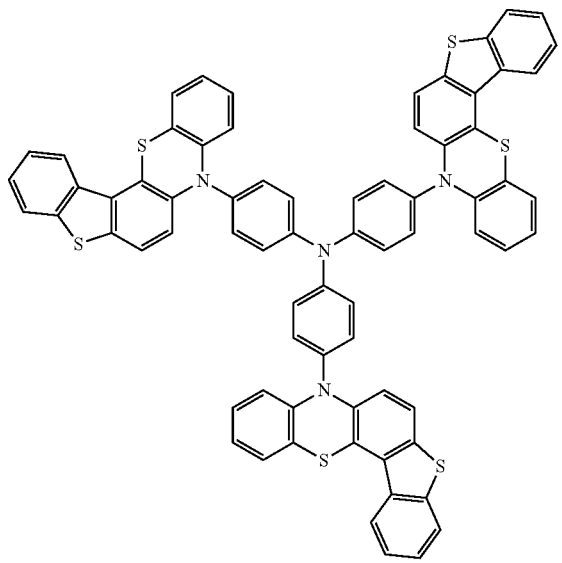
1-21
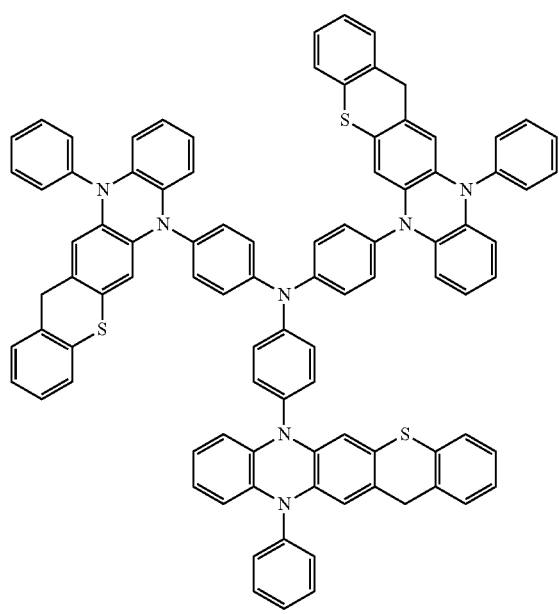
1-22
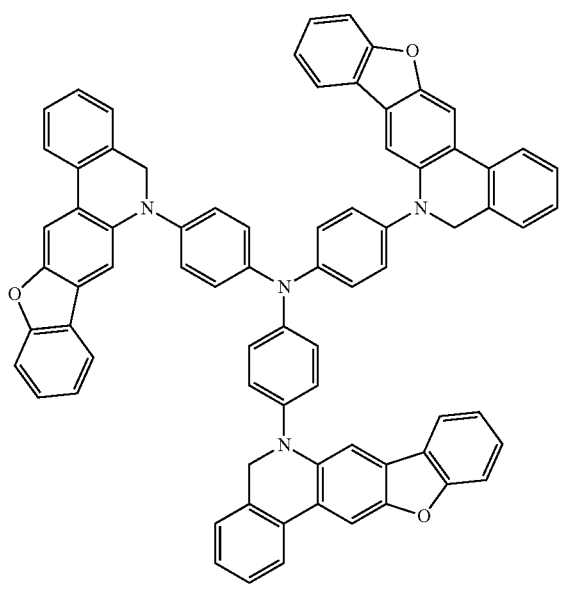

-continued
1-23
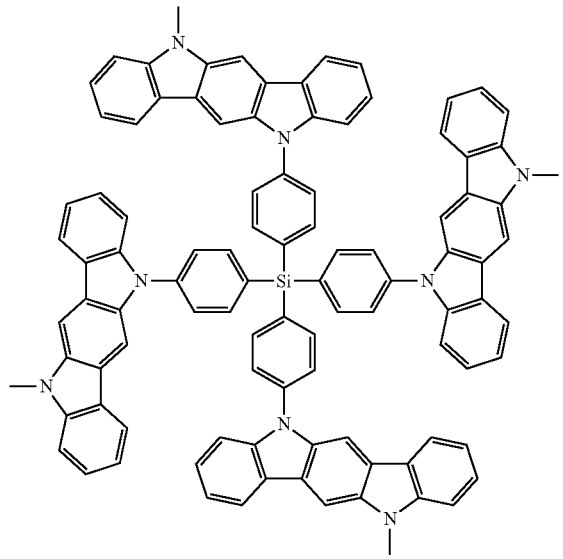
1-24
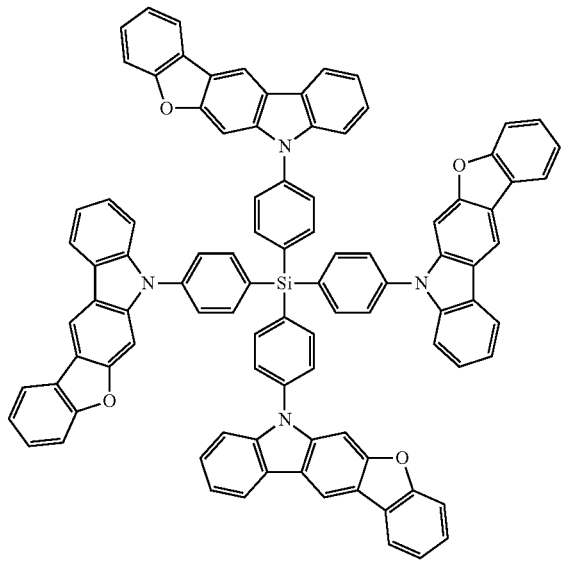
1-25
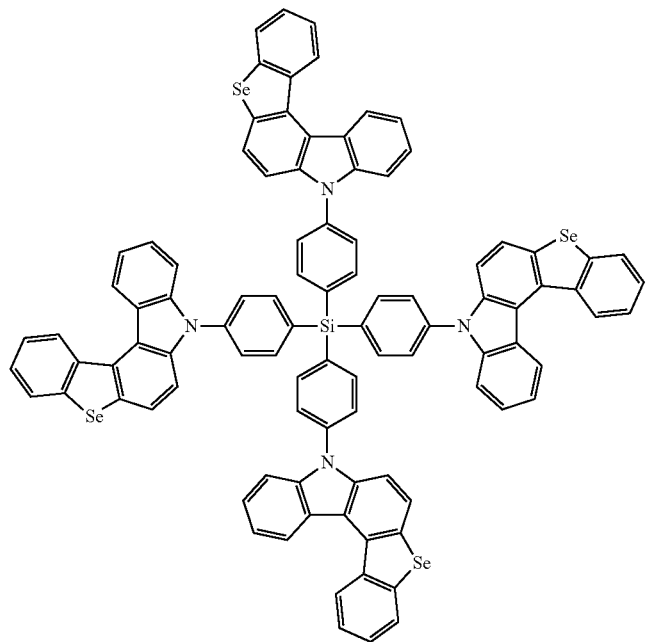

-continued
1-26
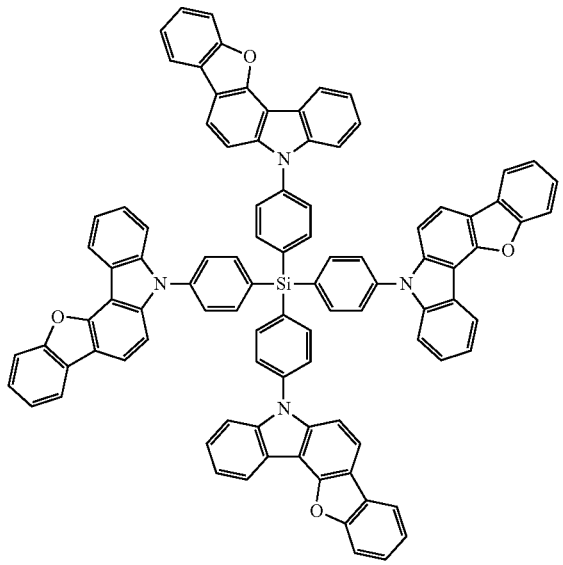
1-27
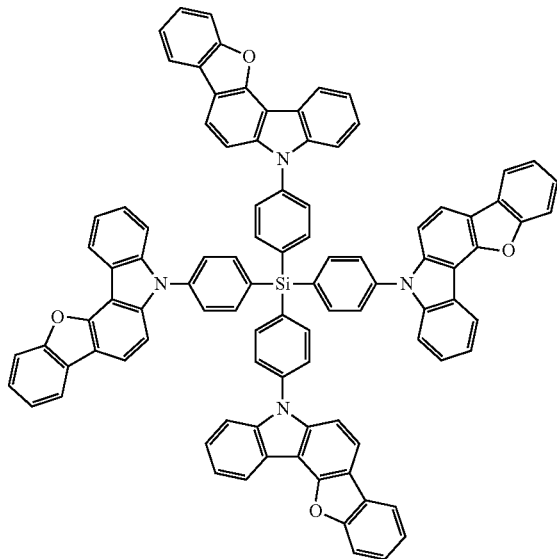
1-28
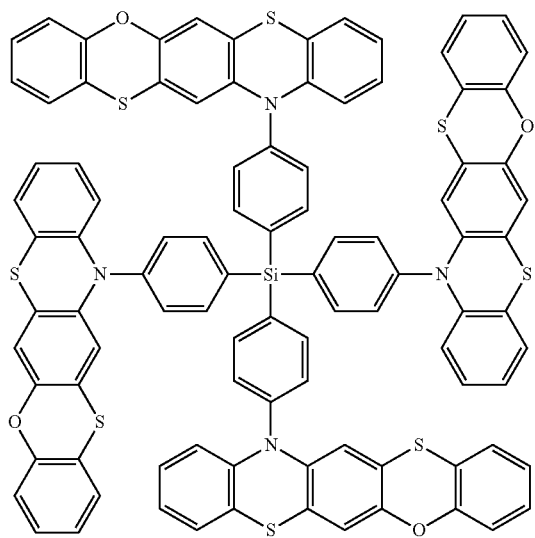

1-29
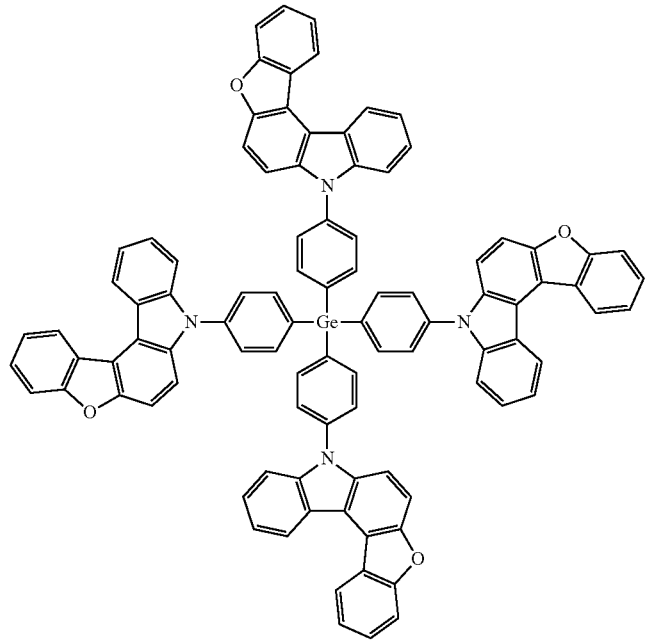
1-30
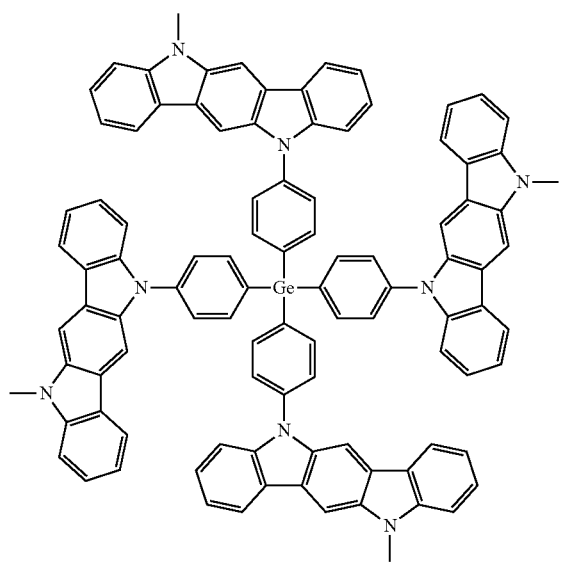
1-31
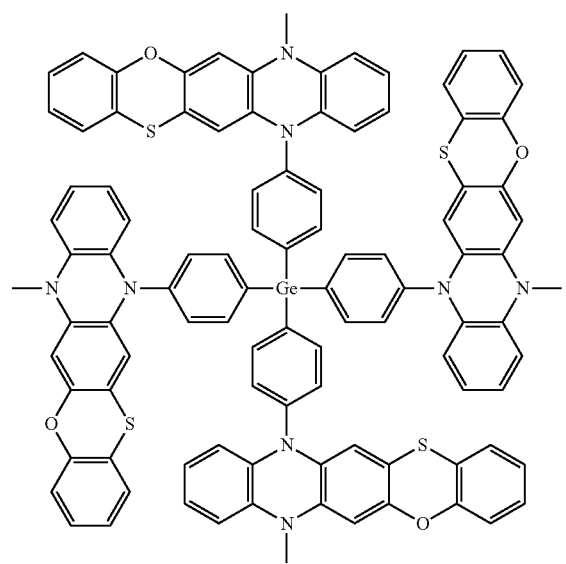

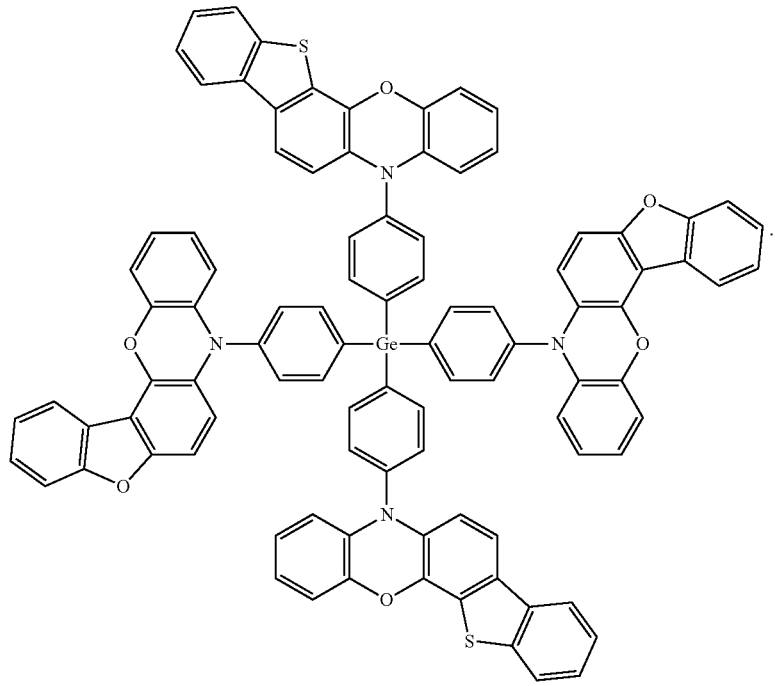
1-32
10. The organic electroluminescent device according to claim 7, wherein the acceptor host material is a compound with the following structures:
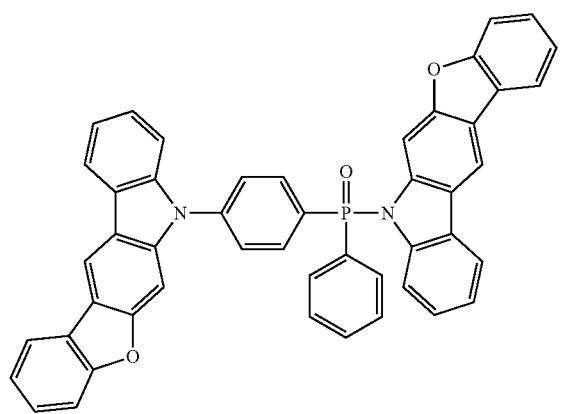
2-1
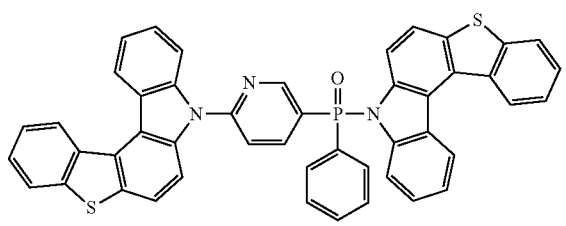
2-2

-continued
2-3
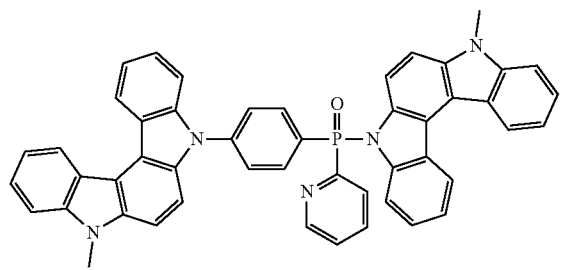
2-4
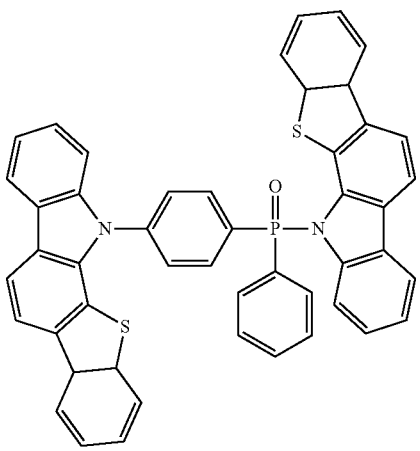
2-5
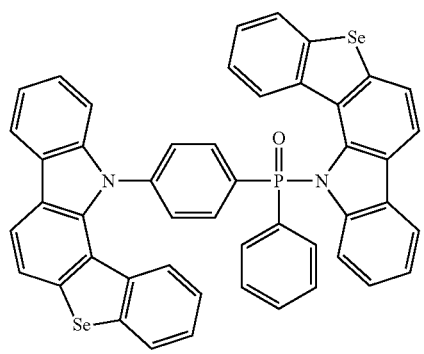
2-6
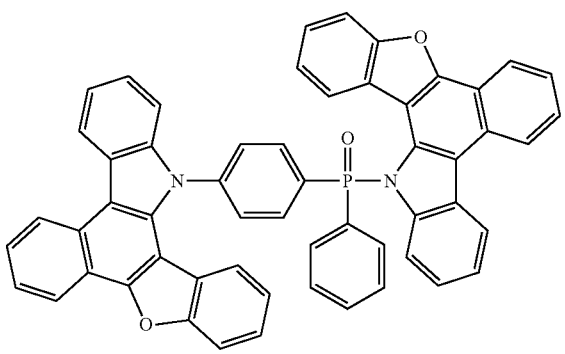
2-7
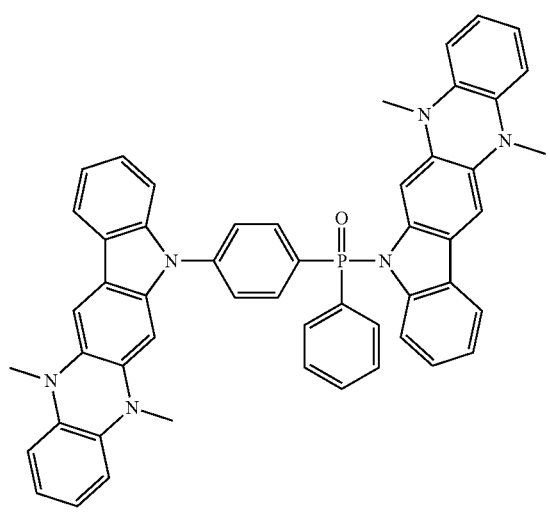
2-8
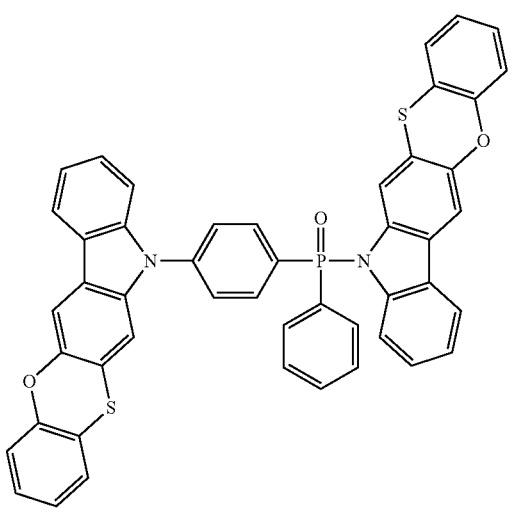

-continued
2-9
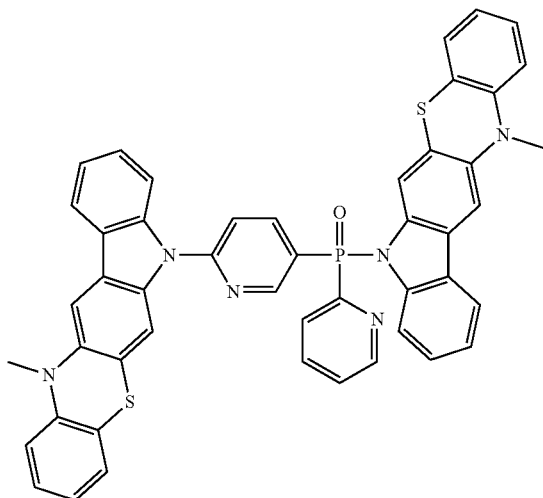
2-10
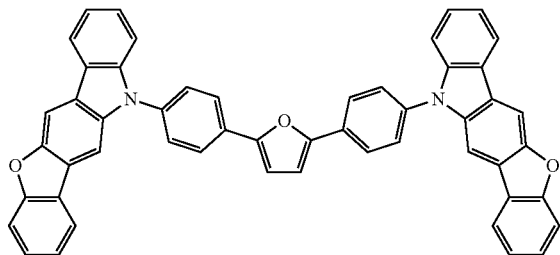
2-11
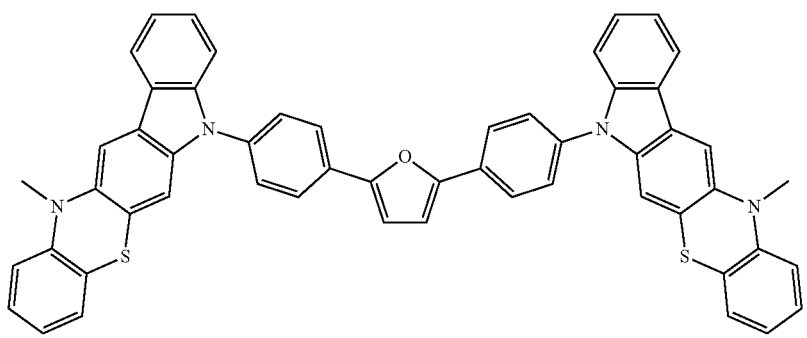
2-12
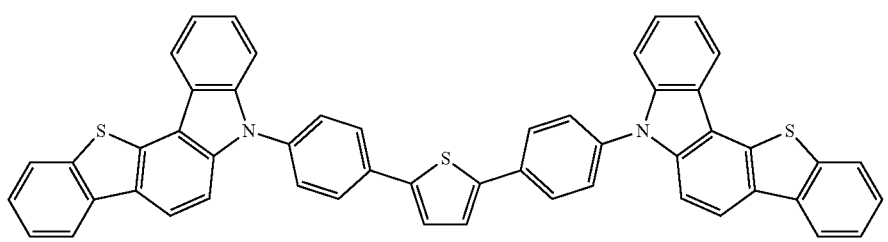
2-13
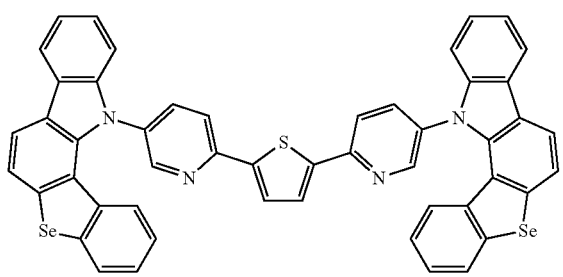
2-14
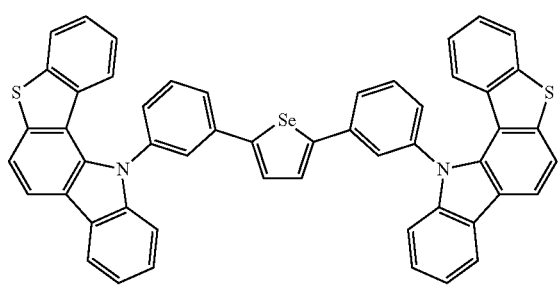

-continued
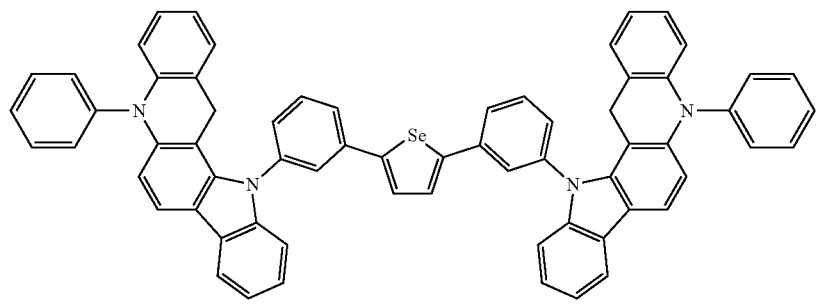
2-15
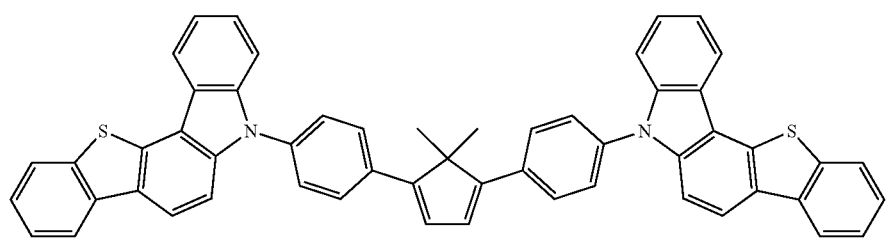
2-16
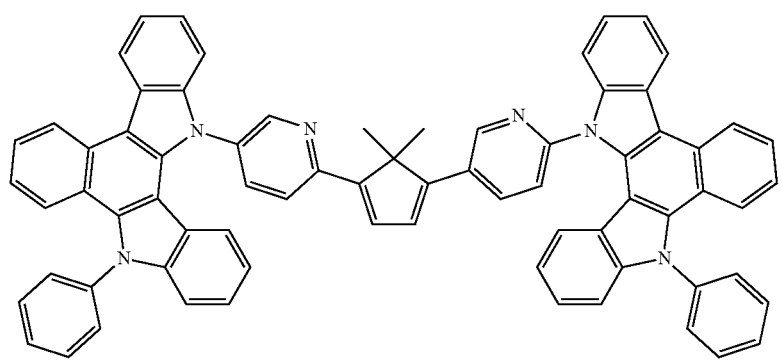
2-17
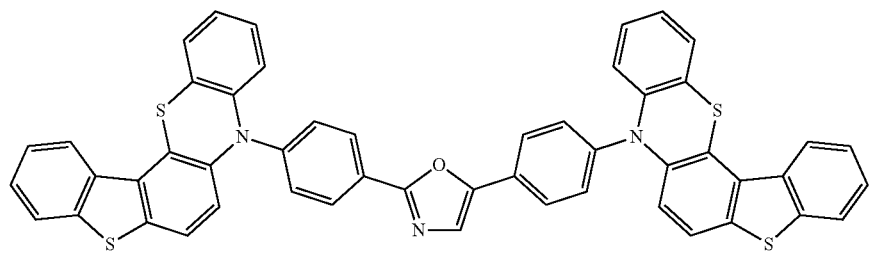
2-18
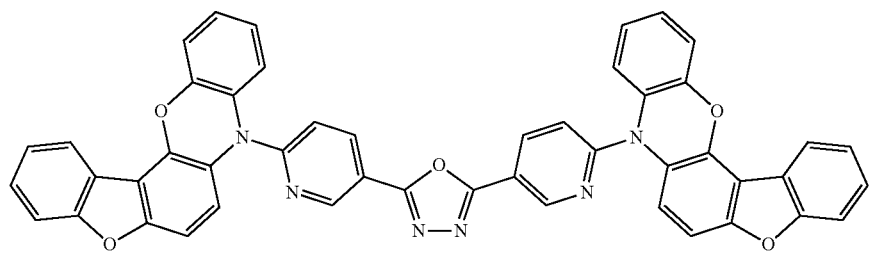
2-19

-continued

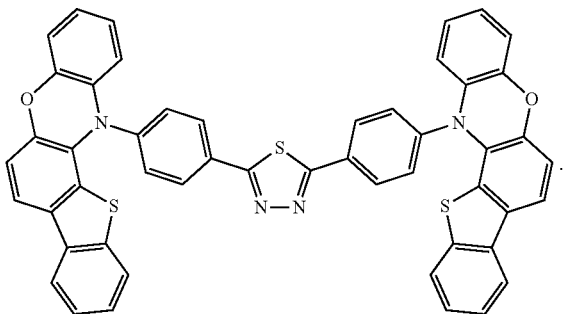

2-20

11. A manufacturing method for an organic electroluminescent device, comprising:

disposing an anode on a substrate;

disposing a light-emitting layer on the anode, a host material of the light-emitting layer being formed by premixing a donor host material and an acceptor host material, the donor host material and the acceptor host material being co-evaporated in a same evaporation source to form an exciplex, and the host material is doped with a guest material; and disposing a cathode on the light-emitting layer, wherein a triplet energy level of the donor host is greater than a singlet energy level of the exciplex, an energy gap between the triplet energy level of the donor host and the singlet energy level of the exciplex is greater than or equal to 0.2 eV; and an absolute value of HOMO energy level of the donor host is less than or equal to 5.3 eV;

a triplet energy level of the acceptor host is greater than a singlet energy level of the exciplex, an energy gap between the triplet energy level of the acceptor host and the singlet energy level of the exciplex is greater than 0.2 eV; and an absolute value of LUMO energy level of the acceptor host is greater than 2.0 eV; and glass transition temperatures of the donor host and the acceptor host are greater than 100° C.

12. The manufacturing method for an organic electroluminescent device according to claim 11, further comprising:

sequentially stacking a hole injection layer and a hole transport layer between the anode and the light-emitting layer; and disposing an optical compensation layer between the hole transport layer and the light-emitting layer.

13. The manufacturing method for an organic electroluminescent device according to claim 11, wherein evaporation temperatures of the donor host and the acceptor host are respectively 150° C.~500° C.

14. The manufacturing method for an organic electroluminescent device according to claim 11, wherein an absolute value of a difference between evaporation temperatures of the donor host and the acceptor host is less than 30° C.

15. The manufacturing method for an organic electroluminescent device according to claim 11, wherein a doping mass ratio of the donor host and the acceptor host is 1:9~9:1.

16. The manufacturing method for an organic electroluminescent device according claim 11, wherein a molecular formula of the donor host material is:

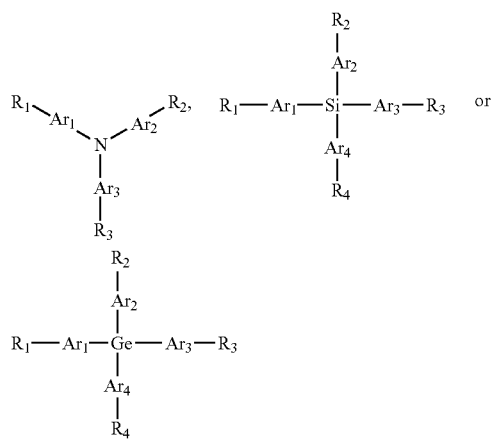

wherein $Ar_1$, $Ar_2$, $Ar_3$ and $Ar_4$ substituents are same or different, and are independently selected from an arylene group or a heteroarylene group; and structures of $R_1$, $R_2$, $R_3$ and $R_4$ are

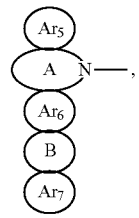

wherein $Ar_5$, A, $Ar_6$, B and $Ar_7$ are connected in a fused ring manner, sharing two atoms, $Ar_5$, $Ar_6$ and $Ar_7$ are the same or different, and are independently selected from a benzene ring, a substituted benzene ring, a naphthalene ring, a substituted naphthalene ring, an anthracene ring or a substituted anthracene ring, A is a five-membered heterocyclic ring or a six-membered heterocyclic ring containing nitrogen atoms, and B is a five-membered ring, a five-membered heterocyclic ring, a six-membered ring or a six-membered heterocyclic ring; and/or, a molecular formula of the acceptor host material is:

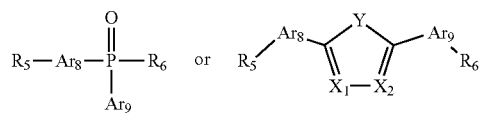

wherein $X_1$ and $X_2$ are same or different, and are —CH— or —N— respectively;
Y is —O—, —S—, —Se—, —C(CH$_3$)$_2$—, —C(C$_6$H$_5$)$_2$— or —C(9-fluorenyl)-;
$Ar_8$ and $Ar_9$ substituents are the same or different, and are independently selected from an arylene group or a heteroarylene group; and structures of $R_5$ and $R_6$ are

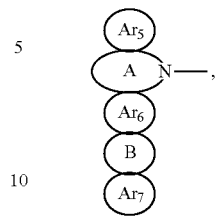

wherein $Ar_{10}$, C ring, $Ar_{11}$, D ring and $Ar_{12}$ are connected in a fused ring manner, sharing two atoms, and $Ar_{10}$, $Ar_{11}$ and $Ar_{12}$ are the same or different, and are independently selected from a benzene ring, a substituted benzene ring, a naphthalene ring or a substituted naphthalene ring, C ring is a five-membered heterocyclic ring or a six-membered heterocyclic ring containing nitrogen atoms, and D ring is a five-membered ring, a five-membered heterocyclic ring, a six-membered ring or a six-membered heterocyclic ring.

* * * * *